United States Patent
Picha et al.

(10) Patent No.: US 11,213,398 B2
(45) Date of Patent: Jan. 4, 2022

(54) HARD-TISSUE IMPLANT COMPRISING A BULK IMPLANT, A FACE, PILLARS, SLOTS, AND AT LEAST ONE SUPPORT MEMBER

(71) Applicant: GARY A. ZWICK, TRUSTEE OF THE EVEREST TRUST UTA APRIL 20, 2017, Cleveland, OH (US)

(72) Inventors: George J. Picha, Brecksville, OH (US); Grant Wesley Phillips, Richfield, OH (US); Rachel Smith, Brecksville, OH (US); James Price, Stow, OH (US); Gregory Causey, Erie, CO (US)

(73) Assignee: Gary A. Zwick, Cleveland, OH (US), Trustee Of The Everest Trust UTA April 20, 2017

( * ) Notice: Subject to any disclaimer, the term of this patent is extended or adjusted under 35 U.S.C. 154(b) by 191 days.

(21) Appl. No.: 16/492,285

(22) PCT Filed: Mar. 8, 2018

(86) PCT No.: PCT/US2018/021499
§ 371 (c)(1),
(2) Date: Sep. 9, 2019

(87) PCT Pub. No.: WO2018/165400
PCT Pub. Date: Sep. 13, 2018

(65) Prior Publication Data
US 2021/0128308 A1    May 6, 2021

Related U.S. Application Data

(60) Provisional application No. 62/469,727, filed on Mar. 10, 2017.

(51) Int. Cl.
*A61F 2/38* (2006.01)
*A61F 2/30* (2006.01)
(Continued)

(52) U.S. Cl.
CPC .......... *A61F 2/30771* (2013.01); *A61F 2/389* (2013.01); *A61F 2/3859* (2013.01);
(Continued)

(58) Field of Classification Search
CPC .................................................. A61F 2/3859
See application file for complete search history.

(56) References Cited

U.S. PATENT DOCUMENTS

| 3,605,123 A | 4/1969 | Hahn |
| 3,808,606 A | 5/1974 | Tronzo |

(Continued)

FOREIGN PATENT DOCUMENTS

| DE | 837294 C | 4/1952 |
| DE | 33 22 803 A1 | 1/1985 |

(Continued)

OTHER PUBLICATIONS

Jain et al., "Advances in Spinal Interbody Cages," Orthop. Surg., vol. 8, p. 278 (abstract only) (Aug. 2016).
(Continued)

*Primary Examiner* — Javier G Blanco
(74) *Attorney, Agent, or Firm* — Pearne & Gordon LLP

(57) ABSTRACT

Hard-tissue implants are provided that include a bulk implant, a face, pillars, slots, and at least one support member. The pillars are for contacting a hard tissue. The slots are to be occupied by the hard tissue. The at least one support member is for contacting the hard tissue. The hard-tissue implant has a Young's modulus of elasticity of at least 3 GPa, and has a ratio of the sum of (i) the volumes of the slots to (ii) the sum of the volumes of the pillars and the volumes of the slots of 0.40:1 to 0.90:1. Methods of making and using hard-tissue implants are also provided.

12 Claims, 28 Drawing Sheets

(51) Int. Cl.

| | | |
|---|---|---|
| *A61F 2/40* | (2006.01) | |
| *A61F 2/42* | (2006.01) | |
| *A61F 2/44* | (2006.01) | |
| *A61L 27/06* | (2006.01) | |
| *A61L 27/18* | (2006.01) | |
| *A61F 2/28* | (2006.01) | |

(52) U.S. Cl.
CPC .......... *A61F 2/4081* (2013.01); *A61F 2/4202* (2013.01); *A61F 2/4261* (2013.01); *A61F 2/442* (2013.01); *A61L 27/06* (2013.01); *A61L 27/18* (2013.01); *A61F 2/2803* (2013.01); *A61F 2002/30069* (2013.01); *A61F 2002/3093* (2013.01); *A61F 2002/30224* (2013.01); *A61F 2002/30326* (2013.01); *A61F 2002/30383* (2013.01); *A61F 2002/30896* (2013.01); *A61F 2002/3863* (2013.01); *A61F 2002/4205* (2013.01); *A61F 2002/4207* (2013.01); *A61F 2310/00017* (2013.01); *A61F 2310/00023* (2013.01); *A61F 2310/00029* (2013.01); *A61F 2310/00293* (2013.01); *A61F 2310/00359* (2013.01); *A61L 2430/02* (2013.01); *A61L 2430/38* (2013.01)

(56) References Cited

U.S. PATENT DOCUMENTS

| | | | |
|---|---|---|---|
| 3,855,638 | A | 12/1974 | Pilliar |
| 4,237,559 | A | 12/1980 | Borom |
| 4,608,052 | A | 8/1986 | Van Kampen et al. |
| 4,834,757 | A | 5/1989 | Brantigan |
| 4,865,603 | A | 9/1989 | Noiles |
| 5,195,892 | A | 3/1993 | Gersberg |
| 5,207,709 | A | 5/1993 | Picha |
| 5,236,453 | A | 8/1993 | Picha |
| 5,263,953 | A | 11/1993 | Bagby |
| 5,312,256 | A | 5/1994 | Scortecci |
| 5,545,226 | A | 8/1996 | Wingo et al. |
| 5,571,185 | A | 11/1996 | Schug |
| 5,628,630 | A | 5/1997 | Misch |
| 5,823,777 | A | 10/1998 | Misch |
| 5,876,457 | A | 3/1999 | Picha et al. |
| 6,001,100 | A | 12/1999 | Sherman et al. |
| 6,071,310 | A | 6/2000 | Picha et al. |
| 6,106,558 | A | 8/2000 | Picha |
| 6,315,562 | B1 | 11/2001 | Kumar |
| 6,346,122 | B1 | 2/2002 | Picha et al. |
| 6,569,201 | B2 | 5/2003 | Moumene et al. |
| 6,789,991 | B2 | 9/2004 | Hsu |
| 6,846,313 | B1 | 1/2005 | Rogers et al. |
| 6,989,032 | B2 | 1/2006 | Errico et al. |
| 7,018,418 | B2 | 3/2006 | Amrich et al. |
| 7,041,140 | B2 | 5/2006 | Picha |
| 7,128,760 | B2 | 10/2006 | Michelson |
| 7,205,051 | B2 | 4/2007 | King et al. |
| 7,250,550 | B2 | 7/2007 | Overby et al. |
| 7,347,873 | B2 | 3/2008 | Paul et al. |
| 7,393,170 | B2 | 7/2008 | Chen |
| 7,556,648 | B2 | 7/2009 | Picha et al. |
| 7,608,107 | B2 | 10/2009 | Michelson |
| 7,691,148 | B2 | 4/2010 | Michelson |
| 7,955,512 | B2 | 6/2011 | Park et al. |
| 8,470,036 | B2 | 6/2013 | Barnes et al. |
| 8,551,173 | B2 | 10/2013 | Lechmann et al. |
| 8,672,940 | B2 | 3/2014 | Prager |
| 8,685,070 | B2 | 4/2014 | Rupp et al. |
| 8,764,831 | B2 | 7/2014 | Lechmann et al. |
| 8,771,354 | B2 | 7/2014 | Picha et al. |
| 8,900,302 | B2 | 12/2014 | Gonzalez-Hernandez |
| 9,198,701 | B2 | 12/2015 | Prien et al. |
| 9,333,081 | B2 | 5/2016 | Picha et al. |
| 9,456,856 | B2 | 10/2016 | Ballard |
| 9,579,206 | B2 | 2/2017 | Picha et al. |
| 9,581,183 | B2 | 2/2017 | Lajewardi et al. |
| 9,801,673 | B2 | 10/2017 | Aeschlimann et al. |
| 9,808,346 | B2 | 11/2017 | Stark |
| 10,154,908 | B2 | 12/2018 | Picha et al. |
| 2001/0039454 | A1 | 11/2001 | Ricci et al. |
| 2002/0040242 | A1 | 4/2002 | Picha et al. |
| 2002/0106393 | A1 | 8/2002 | Bianchi et al. |
| 2004/0093028 | A1 | 5/2004 | Ruff |
| 2004/0122518 | A1 | 6/2004 | Rhoda |
| 2004/0181286 | A1 | 9/2004 | Michelson |
| 2004/0260291 | A1 | 12/2004 | Jensen |
| 2005/0033289 | A1 | 2/2005 | Warren et al. |
| 2005/0049706 | A1 | 3/2005 | Brodke et al. |
| 2005/0246021 | A1 | 11/2005 | Ringeisen et al. |
| 2005/0283158 | A1 | 12/2005 | West |
| 2006/0015184 | A1 | 1/2006 | Winterbottom et al. |
| 2006/0030884 | A1 | 2/2006 | Yeung |
| 2007/0123988 | A1 | 5/2007 | Coughlin |
| 2007/0166124 | A1 | 7/2007 | Hsu |
| 2007/0168037 | A1 | 7/2007 | Posnick |
| 2008/0109037 | A1 | 5/2008 | Steiner |
| 2008/0287910 | A1 | 11/2008 | Picha |
| 2008/0306554 | A1 | 12/2008 | McKinley |
| 2009/0069904 | A1 | 3/2009 | Picha |
| 2009/0105772 | A1 | 4/2009 | Seebeck |
| 2009/0204214 | A1 | 8/2009 | Fuji et al. |
| 2010/0042167 | A1 | 2/2010 | Nebosky et al. |
| 2010/0211118 | A1 | 8/2010 | Christen et al. |
| 2010/0256758 | A1 | 10/2010 | Gordon et al. |
| 2010/0298950 | A1 | 11/2010 | McDonnell et al. |
| 2011/0093020 | A1 | 4/2011 | Wu |
| 2011/0125264 | A1 | 5/2011 | Bagga et al. |
| 2011/0213467 | A1 | 9/2011 | Lozier et al. |
| 2011/0218585 | A1 | 9/2011 | Krinke et al. |
| 2011/0320000 | A1 | 12/2011 | O'Neil et al. |
| 2012/0271427 | A1 | 10/2012 | Serafin |
| 2013/0090735 | A1 | 4/2013 | Mermuys et al. |
| 2013/0110241 | A1 | 5/2013 | Palmatier et al. |
| 2013/0110255 | A1 | 5/2013 | Picha et al. |
| 2013/0116793 | A1 | 5/2013 | Kloss |
| 2013/0325129 | A1 | 12/2013 | Huang |
| 2014/0025181 | A1 | 1/2014 | Vanasse et al. |
| 2014/0180432 | A1 | 6/2014 | Conway et al. |
| 2014/0303729 | A1 | 10/2014 | Lee |
| 2015/0305878 | A1 | 10/2015 | O'Neil et al. |
| 2016/0067048 | A1 | 3/2016 | Hensley et al. |

FOREIGN PATENT DOCUMENTS

| | | |
|---|---|---|
| DE | 103 25 139 A1 | 12/2004 |
| EP | 0 162 604 A1 | 11/1985 |
| EP | 0 269 256 A1 | 6/1988 |
| FR | 3 019 032 A1 | 10/2015 |
| GB | 2181 354 A | 4/1987 |
| WO | 96/40020 A1 | 12/1996 |
| WO | 199640015 A1 | 12/1996 |
| WO | 2002017823 A1 | 3/2002 |
| WO | 2002032345 A2 | 4/2002 |
| WO | 2009022911 A2 | 2/2009 |
| WO | 2009108789 A1 | 9/2009 |
| WO | 2013063069 A1 | 5/2013 |
| WO | 2016018160 A1 | 2/2016 |
| WO | 2016082880 A1 | 6/2016 |
| WO | 2016130878 A1 | 8/2016 |
| WO | 2018053403 A1 | 3/2018 |
| WO | 2018165403 A1 | 9/2018 |
| WO | 2018165405 A1 | 9/2018 |
| WO | 2018169929 A1 | 9/2018 |

OTHER PUBLICATIONS

Chong et al., "The design evolution of interbody cages in anterior cervical discectomy and fusion: a systematic review," BMC Musculoskeletal Disorders, DOI 10.1186/s12891-015-0546-x, pp. 1-11 (Apr. 25, 2015).

Pawtex, "ConnectSPINE TM) PPM (TM) (Porous Paw Metal) Anterior Cervical Interbody Fusion Case (ACIF)," pp. 1-2, avail-

(56) References Cited

OTHER PUBLICATIONS able at http://www.cusmed.com/porous-paw-metal-anterior-cervical-interbody-fusion-cage.html, last accessed Mar. 7, 2018.
Zimmer Biomet, "TM-S Cervial Fusion Device," pp. 1-11, available at http://www.zimmerbiomet.com/medical-professionals/spine/product/tm-s-device.html; last accessed Mar. 7, 2018.
Colton et al., "Screws-Form and Function," AOTrauma (Nov. 2012), pp. 1-10.
Hulbert, S.F., et al.; "Materials of Construction for Artificial Bone Segments"; Research in Dental and Medical Materials (Edward Korostoff ed., 1969), pp. 19-67.
Bobyn, et al.; "Characteristics of bone ingrowth and interface mechanics of a new porous tantalum biomaterial"; The Journal of Bone & Joint Surgery (Br); vol. 81-B, No. 5; Sep. 1999; pp. 907-914.
Itala, A.I., et al.; "Pore Diameter of More Than 100 μm Is Not Requisite for Bone Ingrowth in Rabbits"; 58 Journal of Biomedical Materials Research (Applied Biomaterials); 2001; pp. 679-683.
Briem, D., et al.; "Response of primary fibroblasts and osteoblasts to plasma treated polyetheretherketone (PEEK) surfaces"; 16 Journal of Materials Science Materials in Medicine; 2005; pp. 671-677.
Biomechanics, BME 315; "Elastic anisotropy of bone" (http://silver.neep.wisc.edu/~lakes/BME315N3.pdf—accessed Dec. 8, 2010); p. 1.
Dai, K., "Rational Utilization of the Stress Shielding Effect of Implants"; Biomechanics and Biomaterials in Orthopedics (ed. Dominique G. Poitout, Springer-Verlag London Limited, Singapore, 2004); pages: title, copyright, and 208-215.
McPherson, E.J., "Adult Reconstruction"; Review of Orthopaedics: Expert Consult; Fifth Edition (ed. Mark D. Miller, Saunders Elsevier, U.S , 2008); pp. 312-313, Section 4; "Complications in fixation," subsection a, "Stress shielding."
Bobyn et al., "The Optimum Pore Size for the Fixation of Porous-Surfaced Metal Implants by the Ingrowth of Bone," Clinical Orthopaedics and Related Research, No. 150, pp. 263-270 (1980).
International Search Report and Written Opinion for corresponding International Application No. PCT/US2018/021499 dated May 14, 2018.

HARD-TISSUE IMPLANT COMPRISING A BULK IMPLANT, A FACE, PILLARS, SLOTS, AND AT LEAST ONE SUPPORT MEMBER

CROSS-REFERENCE TO RELATED APPLICATIONS

This application claims the benefit of U.S. Provisional Application No. 62/469,727, filed Mar. 10, 2017, the entire disclosure of which is hereby incorporated herein by reference.

FIELD OF THE INVENTION

The invention relates to hard-tissue implants, and more particularly to hard-tissue implants that include a bulk implant, a face, pillars, slots, and at least one support member.

BACKGROUND OF THE INVENTION

Conventional hard-tissue implants include implants designed to promote ingrowth of hard tissue based on forming a tissue/implant interface in which the implant forms a continuous phase and the tissue forms a discontinuous phase, e.g. based on the implant having a concave and/or porous surface into which the hard tissue can grow, and designed to have add-on surface modifications, e.g. modifications added based on sintering.

For example, Van Kampen et al., U.S. Pat. No. 4,608,052, discloses an implant for use in a human body having an integral attachment surface adapted to permit ingrowth of living tissue. The implant surface is defined by a multiplicity of adjacent, generally concave surface parts having intersecting, generally aligned rims defining an inner attachment surface portion and by a multiplicity of spaced posts projecting from the inner attachment surface. Van Kampen also discloses that implants have been provided with porous surfaces, as described in U.S. Pat. Nos. 3,605,123, 3,808, 606, and 3,855,638.

Also for example, J. D. Bobyn et al, 150 Clinical Orthopaedics & Related Research 263 (1980), discloses that a pore size range of approximately 50 to 400 µm provided an optimal or maximal fixation strength (17 MPa) in the shortest time period (8 weeks) with regard to cobalt-base alloy implants with powder-made porous surfaces. Specifically, implants were fabricated based on coating cylindrical rods of cast cobalt-base alloy with cobalt base alloy powder in four particle size ranges. The particle size ranges were as follows: 25 to 45 µm; 45 to 150 µm; 150 to 300 µm; and 300 to 840 µm. The corresponding pore size ranges of the particles were as follows: 20 to 50 µm; 50 to 200 µm; 200 to 400 µm; and 400 to 800 µm, respectively. The particles were then bonded to the rods based on sintering. All implants were manufactured to have a maximal diameter of 4.5 mm and a length of 9.0 mm. The implants were surgically inserted into holes in dog femurs and bone ingrowth was allowed to proceed. After varying periods of time (4, 8, or 12 weeks), the maximum force required to dislodge the implants was determined. Implants with a pore size lower than 50 µm yielded relatively low fixation strengths at all time points, while implants with a pore size higher than 400 µm exhibited relatively high scatter with regard to fixation strengths, thus indicating that a pore size range of approximately 50 to 400 µm provided an optimal or maximal fixation strength.

Conventional hard-tissue implants also include implants having surface texturing, e.g. raised portions and indented portions, barbs, and/or pillars, to promote an interference fit between the implants and adjacent bone, to make it difficult to withdraw the implants from hard tissue, or to more effectively mechanically anchor at an early date or affix into adjoining hard tissue.

For example, Tuke et al., U.K. Pat. Appl. No. GB2181354A, discloses an orthopedic implant having at least one surface area, integral with the adjacent portion of the implant and adapted in use to contact bone. The surface area has a finely patterned conformation composed of a plurality of raised portions separated from each other by indented portions. The indented portions are of a width and depth to allow bone penetration thereinto in use to promote an interference fit between the implant and adjacent bone in the region of the patterned area.

Also for example, Amrich et al., U.S. Pat. No. 7,018,418, discloses implants having a textured surface with microrecesses such that the outer surface overhangs the microrecesses. In one embodiment, unidirectional barbs are produced in the surface that can be inserted into bone or tissue. The directional orientation of the barbs is intended to make it difficult to withdraw from the bone or tissue.

Also for example, Picha, U.S. Pat. No. 7,556,648, discloses a spinal implant, i.e. an implant for use in fusing and stabilizing adjoining spinal vertebrae, including a hollow, generally tubular shell having an exterior lateral surface, a leading end, and a trailing end. The exterior surface includes a plurality of pillars arranged in a non-helical array. Each pillar has a height of 100 to 4,500 µm and a lateral dimension at the widest point of 100 to 4,500 µm. The exterior surface also has a plurality of holes therethrough to permit bone ingrowth therethrough.

Unfortunately, interfaces of hard tissue and hard-tissue implants in which the hard tissue is in a discontinuous phase may be susceptible to stress shielding, resulting in resorption of affected hard tissue, e.g. bone resorption, over time. Also, addition of surface texturing to implants by sintering can result in the surface texturing occupying an excessive volume of corresponding hard tissue/implant interfaces, leaving insufficient space for hard tissue. In addition, spinal implants are designed to perform under conditions relevant to spine, i.e. compression, rotational shear, and vertical shear, with the compression being essentially constant, the rotational shear being intermittent, and the vertical shear being rare, rather than conditions relevant to other hard tissues such as long bone, maxillary bone, mandibular bone, and membranous bone, i.e. load bearing conditions, including compression and tension, varying across the hard tissue and across time, and intermittent rotational and vertical shear.

Picha et al., U.S. Pat. No. 8,771,354, discloses hard-tissue implants including a bulk implant, a face, pillars, and slots. The hard-tissue implant has a Young's modulus of elasticity of at least 10 GPa, has a ratio of (i) the sum of the volumes of the slots to (ii) the sum of the volumes of the pillars and the volumes of the slots of 0.40:1 to 0.90:1, does not comprise any part that is hollow, and does not comprise any non-pillar part extending to or beyond the distal ends of any of the pillars. The hard-tissue implants can provide immediate load transfer upon implantation and prevent stress shielding over time, thus promoting hard-tissue remodeling and growth at the site of implantation. The interface can have a continuous phase corresponding to the hard tissue and a discontinuous phase corresponding to the hard-tissue implant.

Nonetheless, there remains a need for hard-tissue implants of general applicability that address the issues discussed above and that provide improvements. The hard-tissue implant disclosed herein is such an implant.

BRIEF SUMMARY OF THE INVENTION

A hard-tissue implant is provided that includes a bulk implant, a face, pillars, slots, and at least one support member. The face is an exterior surface of the bulk implant. The pillars are for contacting a hard tissue. The pillars are distributed on the face, across an area of at least 30 mm², and extend distally therefrom. Each pillar is integral to the bulk implant, has a distal end, has a transverse area of (100 μm×100 μm) to (10,000 μm×10,000 μm), i.e. $1.0\times10^4$ μm² to $1.0\times10^8$ μm², and has a height of 100 to 10,000 μm. The slots are to be occupied by the hard tissue. The slots are defined by the pillars. Each slot has a width of 100 to 10,000 μm as measured along the shortest distance between adjacent pillars. The at least one support member also is for contacting the hard tissue. The at least one support member is positioned on the face among the pillars, extends distally from the face, and has a transverse area greater than the transverse area of any of the pillars. The hard-tissue implant has a Young's modulus of elasticity of at least 3 GPa, and has a ratio of (i) the sum of the volumes of the slots to (ii) the sum of the volumes of the pillars and the volumes of the slots of 0.40:1 to 0.90:1.

Also provided is a method of making a hard-tissue implant that, upon implantation into a hard tissue, provides immediate load transfer and prevents stress shielding. The hard-tissue implant is as described above. The method includes designing the hard-tissue implant such that the ratio of (i) the product of (a) the Young's modulus of the hard-tissue implant and (b) the sum of the volumes of the pillars to (ii) the product of (a) the Young's modulus of the hard tissue and (b) the sum of the volumes of the slots will be 0.80:1 to 3.8:1. The method also includes making the hard-tissue implant.

Also provided is a method of use of a hard-tissue implant in a hard tissue of an individual in need thereof. The hard-tissue implant is as described above. The method includes selecting the hard-tissue implant such that the ratio of (i) the product of (a) the Young's modulus of the hard-tissue implant and (b) the sum of the volumes of the pillars to (ii) the product of (a) the Young's modulus of the hard tissue and (b) the sum of the volume of the slots is 0.80:1 to 3.8:1. The method also includes implanting the hard-tissue implant in the hard-tissue.

BRIEF DESCRIPTION OF THE DRAWINGS

These and other features, aspects, and advantages of the present disclosure are better understood when the following detailed description is read with reference to the accompanying drawings, in which.

DETAILED DESCRIPTION

Figure 1:
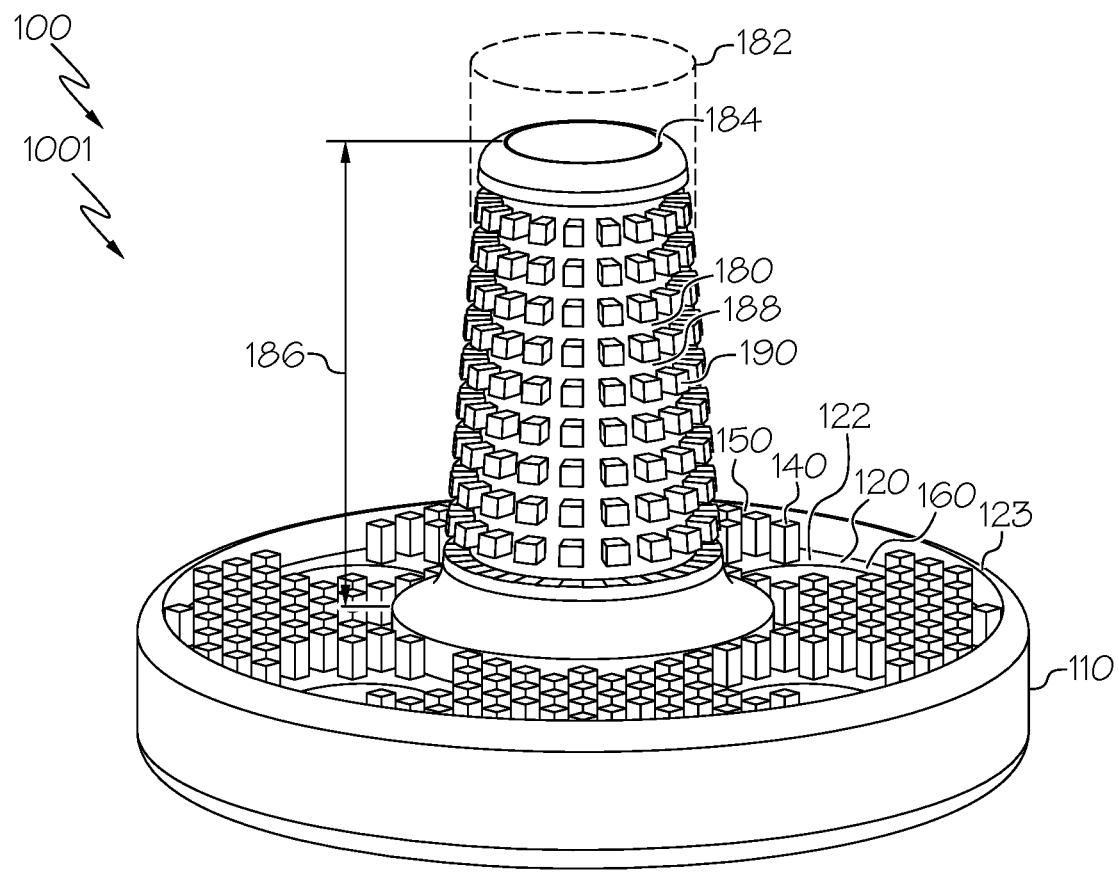
FIG. 1 is a perspective view of a hard-tissue implant corresponding to a glenoid implant for shoulder.

As set forth in the figures, example hard-tissue implants are provided. The hard-tissue implants provide advantages, including for example that the hard-tissue implants can promote hard-tissue remodeling and growth of the hard tissue at the site of implantation and that the interface of the hard-tissue implants and the hard tissue can withstand substantial yield/elongation and load before failure. Without wishing to be bound by theory, it is believed that these advantages are based on properties of the hard-tissue implants and the interface resulting from implantation thereof.

This is because the interface can have a continuous phase corresponding to the hard tissue and a discontinuous phase corresponding to the hard-tissue implant. The hard tissue can also make up at least 40% of the volume of the interface, and the product of the Young's modulus of elasticity of the hard tissue and the volume of the tissue and the product of the Young's modulus of elasticity of the implant and the volume of the pillars of the implant can be well matched. Thus, the interface can exhibit mechanical properties similar to those of the bulk hard tissue adjacent to the interface. Also, the pillars and the at least one support member potentially may be pressed into the hard-tissue, e.g. based on tapping during implantation, potentially eliminating micro-motion and migration of the implant over time, accommodating torque, and/or eliminating the need for adhesives such as cement or grout to hold the implant in place. In addition, the hard-tissue implants may promote rich vascularization of the hard tissue of the interface, enhancing wound healing, providing nutritional support, accelerating healing, remodeling, and integration of the hard tissue, and limiting the potential for infection of the hard tissue. Rapid or immediate integration of the hard tissue into the space between the pillars of the hard-tissue implant may also prevent detrimental cellular reactions at the interface, such as formation of fibrous tissue, seroma, or thrombosis.

It is believed that implantation of the hard-tissue implant will result in the pillars and the at least one support member of the hard-tissue implant contacting the hard tissue. In some cases the pillars and/or the at least one support member may initially penetrate the hard tissue, e.g. partially or completely, upon implantation of the hard-tissue implant. In such cases, the hard-tissue implants can provide immediate load transfer upon implantation and prevent stress shielding over time, thus promoting hard-tissue remodeling and growth at the site of implantation. Alternatively or additionally, in some cases the pillars and/or the at least one support member may penetrate the hard tissue later, under physiological loading. Also alternatively or additionally, over time the hard tissue may grow in and around the pillars, thus occupying slots between the pillars, e.g. during healing.

It also is believed that the hard-tissue implants also provide further advantages in hard-tissue implant applications involving articulation, e.g. for shoulder, wrist, knee, ankle, and spine, because the at least one support member, in combination with the pillars, can prevent pull-out of the hard-tissue implants and further accommodate torque, thus further promoting hard-tissue remodeling and growth at the site of implantation.

The interface resulting from implantation of the hard-tissue implant into the hard tissue will be, or can become, an interface that is continuous with respect to the hard tissue and discontinuous with respect to the hard-tissue implant, across an area of the face of the hard-tissue implant from which the pillars extend. Such an interface will further exhibit properties similar to those of the bulk hard tissue adjacent to the interface, e.g. high resilience to load. The result is that the interface following implantation of a hard-tissue implant into a hard tissue is surprisingly long-lasting and resilient to load.

As used herein, the term "hard-tissue implant" means an implant suitable for implantation in a hard tissue. Exemplary hard-tissue implants include a glenoid implant for shoulder, a distal radius plate implant for wrist, a femoral capture implant for knee, a tibial implant for knee, a tibial implant for ankle, and a talar implant for ankle. Exemplary hard-tissue implants also include an artificial disc implant for spine.

Exemplary hard tissues suitable for implantation of the hard-tissue implants include bone, cartilage, calcified cartilage, non-calcified cartilage, and tissue that has become mineralized. Exemplary hard tissues also include long bone, maxillary bone, mandibular bone, and membranous bone. Exemplary hard tissues also include shoulder, femur, tibia, and talus. Exemplary hard tissues also include spine.

As used herein, the term "pillar" means a projection that extends distally from a surface of a hard-tissue implant, e.g.

from a face of the hard-tissue implant, that is not in direct physical contact with any other pillars or other parts of the implant other than the surface, and that is for contacting a hard tissue. Because a pillar is not in direct physical contact with any other pillars or other parts of the implant other than the surface, upon implantation no pillar forms a continuous phase within the resulting interface of the hard tissue and hard-tissue implant. A pillar can have a transverse area, i.e. an area of a cross-section taken relative to a vertical axis along which the pillar extends distally from the face of the implant, of, for example, (i) (100 µm×100 µm) to (10,000 µm×10,000 µm), i.e. $1.0 \times 10^4$ µm$^2$ to $1.0 \times 10^8$ µm$^2$, (ii) (200 µm×200 µm) to (2,000 µm×2,000 µm), i.e. $4.0 \times 10^4$ µm$^2$ to $4.0 \times 10^6$ µm$^2$, (iii) (250 µm×250 µm) to (1,000 µm×1,000 µm), i.e. $6.3 \times 10^4$ µm$^2$ to $1.0 \times 10^6$ µm$^2$, (iv) (300 µm×300 µm) to (500 µm×500 µm), i.e. $9 \times 10^4$ µm$^2$ to $2.5 \times 10^5$ µm$^2$, (v) (350 µm×350 µm) to (450 µm×450 µm), i.e. $1.2 \times 10^5$ µm$^2$ to $2.0 \times 10^5$ µm$^2$, or (vi) (395 µm×395 µm) to (405 µm×405 µm), i.e. $1.6 \times 10^5$ µm$^2$. Of note, the expression of transverse areas of pillars as squares of linear dimensions, e.g. (100 µm×100 µm), here and throughout this application, is for purposes of convenience only and is not intended to limit any pillars so described to square shapes, square transverse areas, or square cross-sections. A pillar can have a pillar height, i.e. the height of the pillar from the face of the hard-tissue implant to the distal end of the pillar, of, for example, 100 to 10,000 µm, 100 to 5,000 µm, 200 to 2,500 µm, 300 to 1,000 µm, 400 to 600 µm, 450 to 550 µm, 490 to 510 µm, or 500 µm. A pillar can have a volume, i.e. product of pillar transverse area and pillar height, of, for example (i) (100 µm×100 µm×100 µm) to (10,000 µm×10,000 µm×10,000 µm), i.e. $1.0 \times 10^6$ µm$^3$ to $1.0 \times 10^{12}$ µm$^3$, (ii) (200 µm×200 µm×100 µm) to (2,000 µm×2,000 µm×5,000 µm), i.e. $4.0 \times 10^6$ µm$^3$ to $2.0 \times 10^{10}$ µm$^3$, (iii) (250 µm×250 µm×200 µm) to (1,000 µm×1,000 µm×2,500 µm), i.e. $1.3 \times 10^7$ µm$^3$ to $2.5 \times 10^9$ µm$^3$, (iv) (300 µm×300 µm×300 µm) to (500 µm×500 µm×1,000 µm), i.e. $2.7 \times 10^7$ µm$^3$ to $2.5 \times 10^8$ µm$^3$, (v) (350 µm×350 µm×400 µm) to (450 µm×450 µm×600 µm), i.e. $4.9 \times 10^7$ µm$^3$ to $1.2 \times 10^8$ µm$^3$, or (vi) (395 µm×395 µm×490 µm) to (405 µm×405 µm×510 µm), i.e. $7.7 \times 10^7$ µm$^3$ to $8.4 \times 10^7$ µm$^3$. A pillar can have, as seen from a top view, a square shape, a rectangular shape, a herringbone shape, a circular shape, or an oval shape, respectively, or alternatively can have other polygonal, curvilinear, or variable shapes.

As used herein, the term "slot" means the spaces between the pillars. Accordingly, the pillars define the slots. The slots can have a slot height as defined by the pillars, of, for example, 100 to 10,000 µm, 100 to 5,000 µm, 200 to 2,500 µm, 300 to 1,000 µm, 400 to 600 µm, 450 to 550 µm, or 500 µm. The slots can have a slot width as measured along the shortest distance between adjacent pillars of, for example, 100 to 10,000 µm, 100 to 7,500 µm, 100 to 3,000 µm, 150 to 1,000 µm, 175 to 450 µm, 190 to 410 µm, 190 to 210 µm, or 390 to 410 µm. The slots have a volume corresponding to the volume of the space between the pillars.

As used herein, the term "support member" means a projection that extends distally from the face and that has a transverse area greater than the transverse area of any of the pillars. Because the support member has a transverse area greater than the transverse area of any of the pillars, the support member can prevent pull-out of the implants and further accommodate torque. The support member can have a distal end. The support member can have a support member height, i.e. the height of the support member from the face of the hard-tissue implant to the distal end of the support member, that is less than, the same as, or greater than the height of one, many, or all of the pillars. The distal end of the support member can include an opening, e.g. such that the hard-tissue implant has a passage extending from the distal end of the support member, through the support member, and through the bulk implant. Alternatively, the distal end of the support member can lack an opening. The support member can have a support member axial surface. The support member axial surface can be angled with respect to the face of the hard-tissue implant, e.g. being generally transverse with respect to the face of the hard-tissue implant, at 70 to 110 degrees, 80 to 100 degrees, or about 90 degrees. The support member can be, for example, a rod, a tube, a raised rim surrounding a hole, a fin, or a keel, among other structures.

As used herein, the term "pore" refers to a void space of less than 1,000 µm in size, i.e. having a diameter of less than 1,000 µm, on or below a surface, e.g. the surface of a hard-tissue implant. Pores can occur in a material naturally, e.g. based on a natural porosity of the material, or can be introduced, e.g. by chemical or physical treatment. Pores can be continuous with respect to each other, based on being interconnected with each other below a surface, or pores can be discontinuous, based on not being interconnected with each other below a surface. Pores can be sufficiently large to allow for migration and proliferation of osteoblasts and mesenchymal cells. Accordingly, for example, a porous surface is a surface that includes void spaces of less than 1,000 µm in size in the surface, whereas a non-porous surface is a surface that does not include such a void space.

As used herein, the term "interface resulting from implantation of the hard-tissue implant into a hard tissue," or more simply "interface," means the product of implantation wherein the pillars of the hard-tissue implant are contacting a hard tissue and the slots of the hard-tissue implant are occupied, partially or completely, by the hard tissue. The interface includes the pillars, hard tissue that occupies the slots of the hard-tissue implant, any remaining unoccupied space in the slots, any hard tissue that occupies any additional space between the face of the implant and a plane defined by the distal ends of the pillars, and any hard tissue that occupies any pores on the face or the pillars. Accordingly, the interface boundaries are the face of the hard tissue implant, the internal surfaces of any pores on the face, and the bulk tissue surrounding interface.

In some example embodiments, e.g. immediately after implanting the hard-tissue implant with at least some penetration of the pillars into the hard tissue and/or after at least some remodeling and growth of the hard tissue to partially fill in space between the hard-tissue implant and the hard tissue, the pillars are contacting the hard tissue (e.g. at distal ends of the pillars), and the slots are partially occupied by the hard tissue. In other example embodiments, e.g. immediately after implanting the hard-tissue implant with extensive penetration of the pillars into the hard-tissue and/or after extensive remodeling and growth of the hard tissue to fill in all space between the hard-tissue implant and the hard tissue, the pillars are contacting the hard tissue (e.g. at distal ends and lateral surfaces of the pillars), and the slots are completely occupied by the hard tissue. In other example embodiments, the pillars contact the hard tissue over time, based on remodeling and growth of hard tissue in and around the pillars, e.g. during healing.

As used herein, the term "continuous," when used for example in reference to the hard-tissue of an interface, means that the hard tissue forms a single continuous phase, extending throughout and across the interface to each boundary of the interface. As used herein, the term "discontinuous," when used for example in reference to the hard-tissue implant of an interface, means that the hard-tissue implant does not form such a single continuous phase.

Hard-Tissue Implant

Considering the features of an example hard-tissue implant in more detail, FIGS. 1-7 provide illustrations in perspective view of various example hard-tissue implants 100, corresponding to a glenoid implant for shoulder 1001, a distal radius plate implant for wrist 1002, a femoral capture implant for knee 1003, a tibial implant for knee 1004, a tibial implant for ankle 1005, a talar implant for ankle 1006, and an artificial disc implant for spine 1007. Additional views of the glenoid implant for shoulder 1001 are shown in FIGS. 14-18. Additional views of the distal radius plate implant for wrist 1002 are shown in FIGS. 19-24. Additional views of the femoral capture implant for knee 1003 are shown in FIGS. 25-32. Additional views of the tibial implant for knee 1004 are shown in FIGS. 33-37. Additional views of the tibial implant for ankle 1005 are shown in FIGS. 38-44. Additional views of the talar implant for ankle 1006 are shown in FIGS. 45-51.

The hard-tissue implant 100 can be made from a material having a Young's modulus of elasticity, i.e. a tensile modulus of elasticity, of at least 3 GPa, as measured at 21° C. The hard-tissue implant 100 can be made, for example, from one or more materials such as implantable-grade polyaryletherketone that is essentially unfilled (such as implantable-grade polyetheretherketone or implantable-grade polyetherketoneketone), titanium, stainless steel, cobalt-chromium alloy, titanium alloy (such as Ti-6A1-4V titanium alloy or Ti-6A1-7Nb titanium alloy), ceramic material (such as silicon nitride (Si3N4)), or implantable-grade composite material (such as implantable-grade polyaryletherketone with filler, implantable-grade polyetheretherketone with filler, implantable-grade polyetheretherketone with carbon fiber, or implantable-grade polyetheretherketone with hydroxyapatite). Specific examples include (i) implantable-grade polyetheretherketone that is essentially unfilled, which has a Young's modulus of approximately 4 GPa, (ii) implantable-grade polyetheretherketone with filler, e.g. carbon-fiber-reinforced implantable-grade polyetheretherketone, which has a Young's modulus of elasticity of at least 18 GPa, (iii) titanium, which has a Young's modulus of elasticity of approximately 110 GPa, (iv) stainless steel, which has a Young's modulus of elasticity of approximately 200 GPa, (v) cobalt-chromium alloy, which has a Young's modulus of elasticity of greater than 200 GPa, or (vi) titanium alloy, which has a Young's modulus of elasticity of approximately 105-120 GPa, all as measured at 21° C. The hard-tissue implant 100 also can be made, for example, from one or more hard tissues such as a hard tissue obtained from a human or animal (such as autologous hard tissue, allogenic hard tissue, or xenogeneic hard tissue), human cartilage, animal cartilage, human bone, animal bone, cadaver bone, or cortical allograft. Such hard tissues obtained from a human or animal can have a Young's modulus of elasticity of, e.g. 4 to 18 GPa. Such hard tissues obtained from a human or animal can also be treated, in advance of implantation, to decrease or eliminate the capacity of the hard tissue to elicit an immune response in an individual upon implantation into the individual. The hard-tissue implant 100 also can be made, for example, from one or more materials such as resin for rapid prototyping, SOMOS® NanoTool non-crystalline composite material, SOMOS® 9120 liquid photopolymer, SOMOS® WaterShed XC 11122 resin, ACCURA® XTREME™ White 200 plastic, or ACCURA® 60) plastic. The hard-tissue implant 100 also can be made from further combinations of the above-noted materials and/or hard tissues. Accordingly, the hard-tissue implant 100 has a Young's modulus of elasticity of at least 3 GPa, for example 18 to 230 GPa, 18 to 25 GPa, 100 to 110 GPa, 190 to 210 GPa, 200 to 230 GPa, 105 to 120 GPa, or 4 to 18 GPa.

As shown in FIGS. 1-7, the hard-tissue implant 100 includes a bulk implant 110, a face 120, pillars 140, slots 150, and at least one support member 180.

Figure 8:
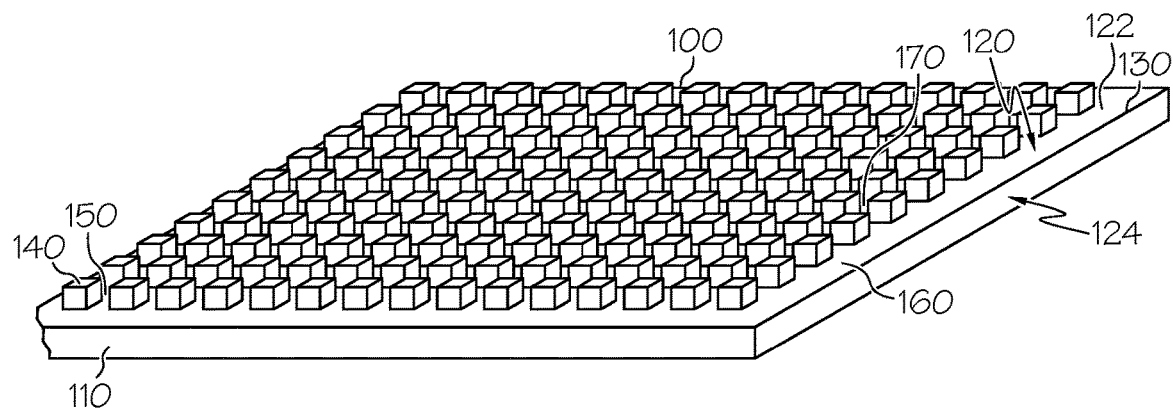
FIG. 8 is a schematic perspective view of a portion of a hard-tissue implant including pillars.

Considering the bulk implant 110 in more detail, as shown in FIG. 8, the bulk implant 110 forms the core of the hard-tissue implant 100 and can have a three-dimensional rectangular prism shape, although cuboidal, cylindrical, pyramidal, conical, and other three-dimensional shapes may be used in further examples. The bulk implant 110 can be made from one or more of the materials or hard tissues noted above with respect to the implant 100, e.g. one or more materials such as implantable-grade polyaryletherketone that is essentially unfilled (such as implantable-grade polyetheretherketone or implantable-grade polyetherketoneketone), titanium, stainless steel, cobalt-chromium alloy, titanium alloy (such as Ti-6Al-4V titanium alloy or Ti-6Al-7Nb titanium alloy), ceramic material (such as silicon nitride (Si3N4)), or implantable-grade composite material (such as implantable-grade polyaryletherketone with filler, implantable-grade polyetheretherketone with filler, implantable-grade polyetheretherketone with carbon fiber, or implantable-grade polyetheretherketone with hydroxyapatite), or e.g. one or more hard tissues such as a hard tissue obtained from a human or animal (such as autologous hard tissue, allogenic hard tissue, or xenogeneic hard tissue), human cartilage, animal cartilage, human bone, animal bone, cadaver bone, or cortical allograft, or e.g. one or more materials such as resin for rapid prototyping, SOMOS® NanoTool non-crystalline composite material, SOMOS® 9120 liquid photopolymer, SOMOS® WaterShed XC 11122 resin, ACCURA® XTREME™ White 200 plastic, or ACCURA® 60) plastic.

The bulk implant 110 can be porous or non-porous. For example, the bulk implant 110 can include one or more surfaces that are porous, and/or can be made from one or more materials that are porous. Such porous surfaces can include pores having diameters of, e.g. 1 to 900 µm, 100 to 800 µm, or 200 to 600 µm. Also for example, the bulk implant 110 can include only surfaces that are non-porous, and/or can be made only from one or more materials that are non-porous.

Considering now the face 120 in more detail, as shown in FIG. 1 and FIG. 8, the face 120 of the hard-tissue implant 100 is an exterior surface of the bulk implant 110, having a total area 160, not including area occupied by the at least support member 180. As shown in FIG. 8, the face 120 can be flat, i.e. have a flat contour. Alternatively, the face 120 can be cylindrical, i.e. have a cylindrical contour. As further alternatives, the face 120 can have other angular, curvilinear, and/or irregular contours. The face 120 can have a rectangular peripheral shape as seen from a top view, although other polygonal, curvilinear, or other shapes may be used in further examples. As shown in FIG. 8, the face can be defined by an edge 130. For example, the edge 130 can be a single continuous edge that defines the face 120. Also for example, the edge 130 can be two edges that are discontinuous with respect to each other that together define the face 120. Also for example, the edge 130 can be three or more edges that are discontinuous with respect to each other that together define the face 120. As shown in FIG. 8, the edge 130 and the pillars 140 closest to the edge 130 can define a peripheral border 122 of the face 120. As shown in FIG. 1, the edge 130 can include a raised wall 123 that extends above the face 120, such that the face 120 is recessed with respect to the raised wall 123. As shown in FIG. 8, the edge 130 can define an intersection between the face 120 and one or more adjacent faces 124 of the hard-tissue implant 100. The face 120 and the one or more adjacent faces 124 may intersect at the edge 130 at a right angle, although the face 120 and the one or more adjacent faces 124 may also intersect at other angles, e.g. acute angles, obtuse angles, or varying angles. The edge 130 can be sharp, although other rounded, angular, smooth, and/or irregular edges may be used in further examples. The face 120 can be porous, e.g. including pores having diameters of, e.g. 1 to 900 µm, 100 to 800 µm, or 200 to 600 µm, or the face 120 can be non-porous. The bulk implant 110 can include more than one face 120, e.g. two, three, four, five, or more faces 120.

Considering now the pillars 140 in more detail, the pillars 140 are for contacting a hard tissue. The hard tissue can be selected, for example, from the group consisting of bone, cartilage, calcified cartilage, non-calcified cartilage, and tissue that has become mineralized. The hard tissue can also be selected, for example, from the group consisting of long bone, maxillary bone, mandibular bone, and membranous bone. The hard tissue can also be selected, for example, from the group consisting of shoulder, femur, tibia, and talus. The hard tissue can also be, for example, spine. In some examples, the pillars 140 may contact a hard tissue immediately upon implantation, e.g. based on extending distally from a face 120 of the hard-tissue implant 100. In some examples, the pillars 140 may contact a hard tissue over time after implantation, e.g. based on remodeling and growth of a hard tissue to come in contact with pillars 140 for which distal ends 430 of the pillars 140 are recessed relative to a surrounding surface of the hard-tissue implant 100.

Figure 9:
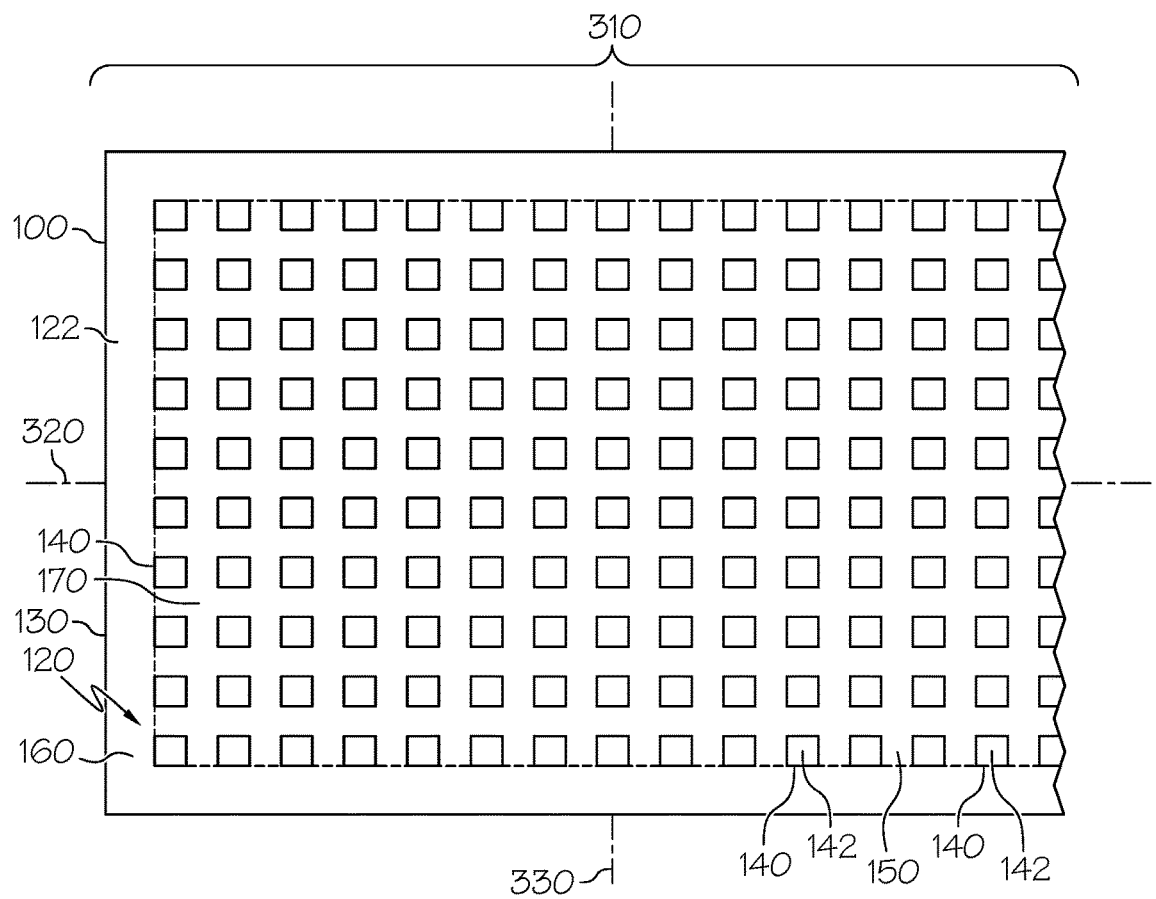
FIG. 9 is a schematic top plan view of a portion of a hard-tissue implant including pillars.

As shown in FIG. 9, the pillars 140 are distributed on the face 120 of the hard-tissue implant 100, across an area 170 of the face 120 of at least 30 mm². For example, the pillars 140 can be distributed in a regular pattern 310 on the face 120 of the hard-tissue implant 100, across the area 170 of the face 120. In this regard, the pillars 140 can be distributed in even rows along a horizontal axis 320 and a vertical axis 330 of the face 120, and can be distributed along a given row uniformly with respect to the distances between the centers 142 of the pillars 140 in the row. Also for example, the pillars 140 can also be distributed in other regular patterns, e.g. the pillars 140 can be distributed in rows that are even with respect to the horizontal axis 320 but not the vertical axis 330, or vice versa, the pillars 140 in one row may be offset from the pillars 140 in adjacent rows, the pillars 140 may be arranged in a spiral pattern, etc. Also for example, the pillars 140 can be distributed on the face 120 of the hard-tissue implant 100 in irregular patterns or randomly. For example, the pillars 140 can be distributed on the face 120 of the hard-tissue implant 100 such that the pillars 140 are packed more densely on one area of the face 120 and less densely on another area of the face 120. Moreover, for a bulk implant 110 including more than one face 120 across which pillars 140 are distributed, the pillars 140 can be distributed differently on the various faces 120, e.g. in different regular patterns 310, in different irregular patterns, and/or packed at different densities.

As shown in FIG. 8 and FIG. 9, the pillars 140 can be distributed on the face 120 of the hard-tissue implant 100 such that none of the pillars 140 are located at an edge 130, i.e. the face 120 can have a peripheral border 122 that is not occupied by any pillars 140, resulting in the area 170 of the face 120 across which the pillars 140 are distributed being less than the total area 160 of the face 120. In other example embodiments the pillars 140 can be distributed on the face 120 of the hard-tissue implant 100 such that at least some of the pillars 140 are located at an edge 130, e.g. the area 170 of the face 120 across which the pillars 140 are distributed can be equal to the total area 160 of the face 120.

Figure 10:
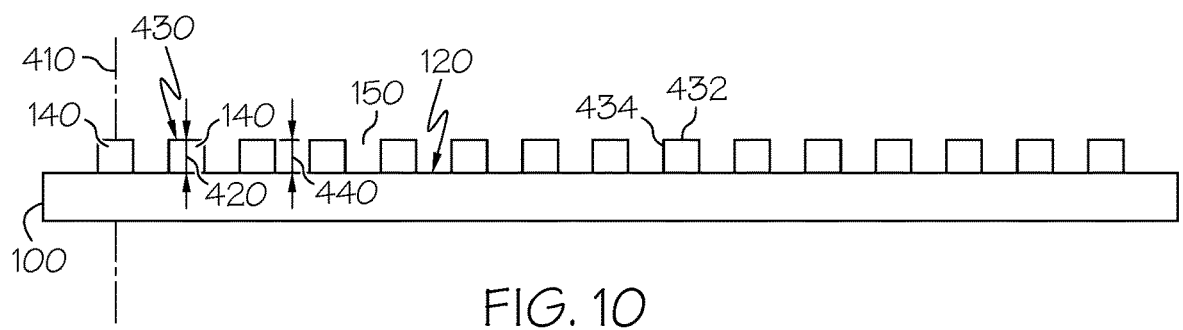
FIG. 10 is a schematic side elevational view of a portion of a hard-tissue implant including pillars.

As shown in FIG. 10, the pillars 140 extend distally from the face 120 of the hard-tissue implant 100. For example, the pillars 140 can extend distally along a vertical axis 410 from the face 120 of the hard-tissue implant 100. As shown, the pillars 140 can extend in a uniform direction, i.e. all pillars 140 extend distally at the same angle with respect to the face 120 and in the same direction. Also for example, some pillars 140 may extend distally at a different angle and/or in a different direction relative to other pillars 140, for example for a hard-tissue implant 100 for which the face 120 is not flat. As also shown, the pillars 140 can be perpendicular to the face 120, e.g. extending perpendicularly from the face 120. Also for example, the pillars 140 can extend from the face 120 at other angles and/or varying angles.

As shown in FIG. 8, each pillar 140 is integral to the bulk implant 110, i.e. the pillars 140 and the bulk implant 110 are made from the same starting material, rather than, for example, the pillars 140 being an add-on to the bulk implant 110. Like the bulk implant 110, the pillars 140 can be porous, e.g. including pores having diameters of, e.g. 1 to 900 µm, 100 to 800 µm, or 200 to 600 µm, or the pillars 140 can be non-porous.

As shown in FIG. 10, each pillar 140 has a distal end 430, corresponding to the distal-most portion of the pillar 140 relative to the face 120 of the hard-tissue implant 100. Each pillar 140 can have distal edges 432, corresponding to edges defining the distal end 430 of each pillar 140. Each pillar 140 can also have lateral edges 434, corresponding to edges of the lateral sides of each pillar 140. The distal edges 432 and/or the lateral edges 434 can be sharp, although other rounded, angular, smooth, and/or irregular edges may be used in further examples.

Figure 3:
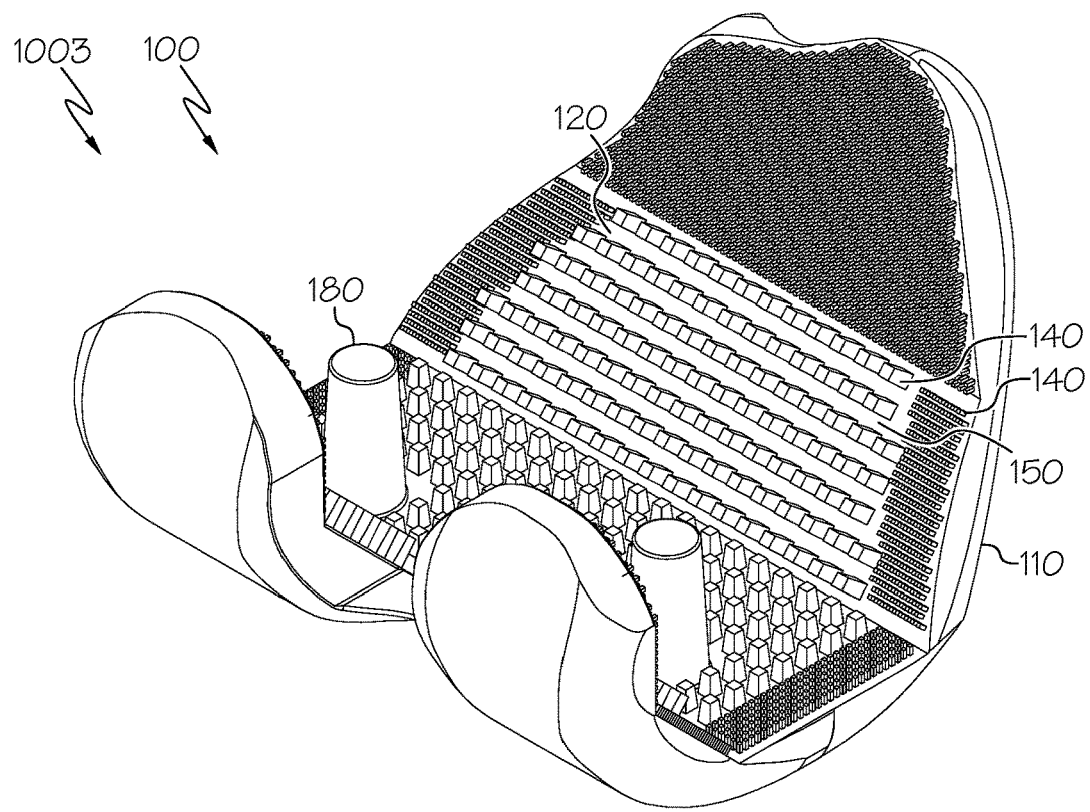
FIG. 3 is a perspective view of a hard-tissue implant corresponding to a femoral capture implant for knee.
Figure 11A:
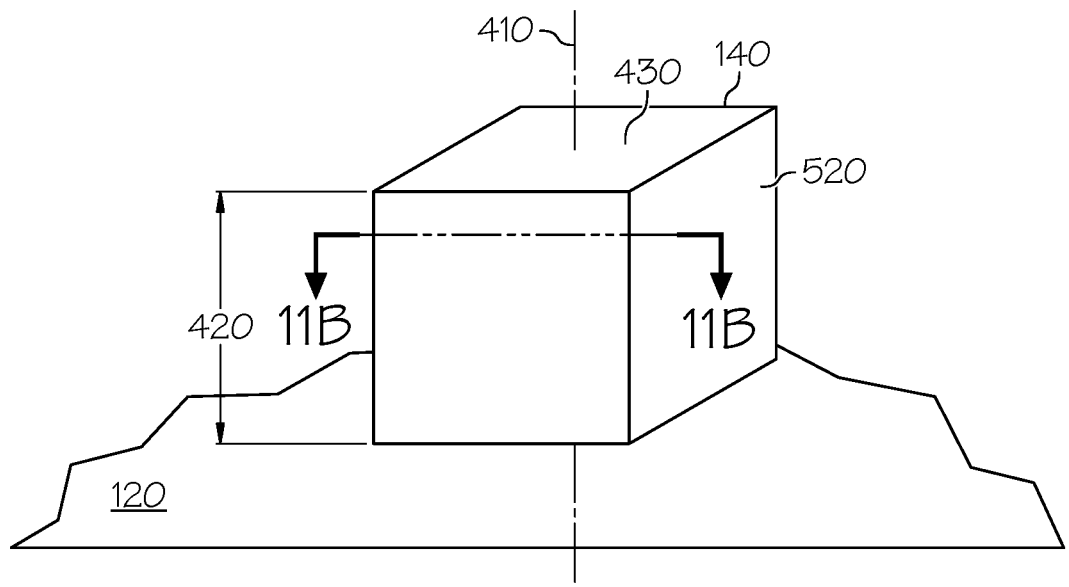
FIG. 11A is a schematic perspective view of a pillar of a hard-tissue implant.
Figure 11B:
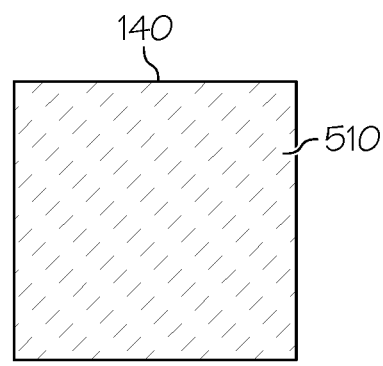
FIG. 11B is a schematic cross-sectional view of a pillar of a hard-tissue implant.
Figure 12A:
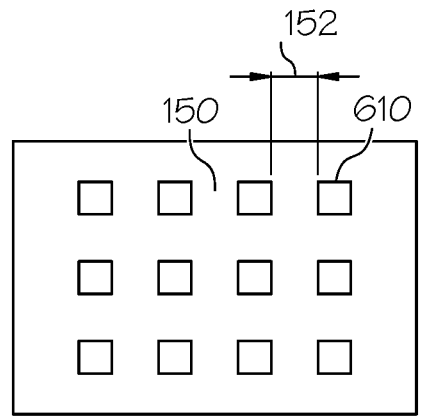
FIGS. 12A-E are schematic top plan views of portions of hard-tissue implant including pillars in which the circumference of the transverse area of the pillars thereof have (A) a square shape, (B) a rectangular shape, (C) a herringbone shape, (D) a circular shape, and (E) an oval shape.
Figure 12B:
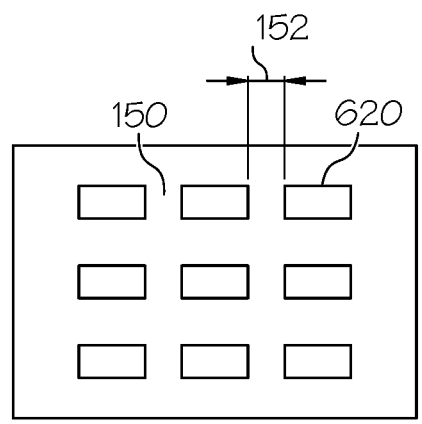
Figure 12C:
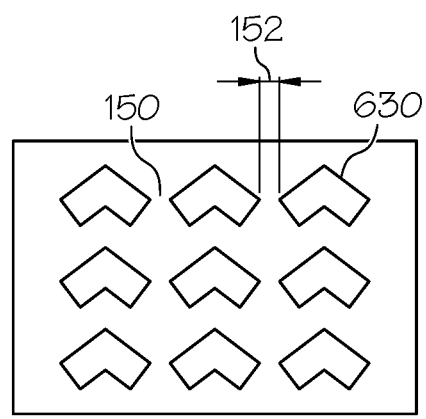
Figure 12D:
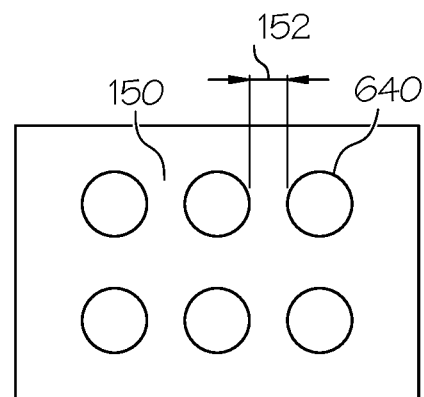
Figure 12E:
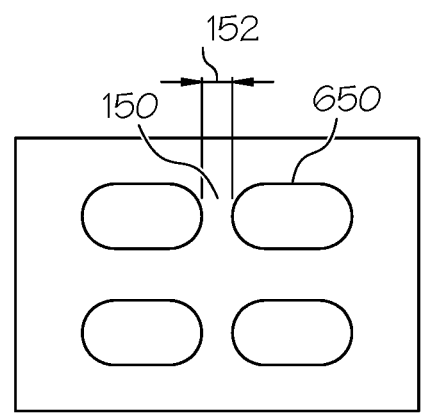

With respect to dimensions of the pillars 140, as shown in FIG. 11A and FIG. 11B, each pillar 140 has a transverse area 510, i.e. an area of a cross-section taken relative to the vertical axis 410 along which the pillar 140 extends distally from the face 120, of, for example, (i) (100 µm×100 µm) to (10,000 µm×10,000 µm), i.e. $1.0 \times 10^4$ µm² to $1.0 \times 10^8$ (ii) (200 µm×200 µm) to (2,000 µm×2,000 µm), i.e. $4.0 \times 10^4$ µm² to $4.0 \times 10^6$ µm², (iii) (250 µm×250 µm) to (1,000 µm×1,000 µm), i.e. $6.3 \times 10^4$ µm² to $1.0 \times 10^6$ µm², (iv) (300 µm×300 µm) to (500 µm×500 µm), i.e. $9 \times 10^4$ µm² to $2.5 \times 10^5$ µm², (v) (350 µm×350 µm) to (450 µm×450 µm), i.e. $1.2 \times 10^5$ µm² to $2.0 \times 10^5$ µm², or (vi) (395 µm×395 µm) to (405 µm×405 µm), i.e. $1.6 \times 10^5$ µm². As shown in FIG. 10 and FIG. 11B, each pillar 140 has a pillar height 420, i.e. the height of the pillar 140 from the face 120 of the hard-tissue implant 100 to the distal end 430 of the pillar 140, of, for example, 100 to 10,000 µm, 100 to 5,000 µm, 200 to 2,500 µm, 300 to 1,000 µm, 400 to 600 µm, 450 to 550 µm, 490 to 510 µm, or 500 µm. As shown in FIG. 11A, each pillar 140 has a volume 520, i.e. product of pillar transverse area 510 and pillar height 420, of, for example (i) (100 µm×100 µm×100 µm) to (10,000 µm×10,000 µm×10,000 µm), i.e. $1.0 \times 10^6$ µm³ to $1.0 \times 10^{12}$ µm³, (ii) (200 µm×200 µm×100 µm) to (2,000 µm×2,000 µm×5,000 µm), i.e. $4.0 \times 10^6$ µm³ to $2.0 \times 10^{10}$ (iii) (250 µm×250 µm×200 µm) to (1,000 µm×1,000 µm×2,500 µm), i.e. $1.3 \times 10^7$ µm³ to $2.5 \times 10^9$ µm³, (iv) (300 µm×300

μm×300 μm) to (500 μm×500 μm×1,000 μm), i.e. 2.7×10$^7$ μm$^3$ to 2.5×10$^8$ (v) (350 μm×350 μm×400 μm) to (450 μm×450 μm×600 μm), i.e. 4.9×10$^7$ μm$^3$ to 1.2×10$^8$ μm$^3$, or (vi) (395 μm×395 μm×490 μm) to (405 μm×405 μm×510 μm), i.e. 7.7×10$^7$ μm$^3$ to 8.4×10$^7$ μm$^3$. As shown in FIG. 1 and FIG. 8, the pillars 140 extending from the face 120 can, for example, all have identical dimensions, e.g. identical pillar transverse areas 510, pillars heights 420, and thus identical individual volumes. Alternatively, as shown in FIG. 3, one or more pillars 140 can have dimensions that differ from those of other pillars 140, such that the pillar transverse areas 510 and/or pillar heights 420, and thus volumes, of the one or more pillars 140 differ from those of the other pillars 140. As shown in FIG. 1, for a hard-tissue implant 100 that includes a raised wall 123, the pillar height 420 can be the same as a height of the raised wall 123, or alternatively the pillar height 420 can be less than, greater than, or variable with respect to, a height of the raised wall 123.

Turning to FIG. 12A to FIG. 12E, the pillars 140 can have, as seen from a top view, a square shape, a rectangular shape, a herringbone shape, a circular shape, or an oval shape, or alternatively can have other polygonal, curvilinear, or variable shapes. For example, in some embodiments all pillars 140 can have the same shape, e.g. a square shape, a rectangular shape, a herringbone shape, a circular shape, or an oval shape, as seen from a top view. Also for example, in some embodiments not all pillars 140 have the same shape as seen from a top view.

Considering now the slots 150 in more detail, the slots 150 are to be occupied by the hard tissue. For example, upon implantation of the hard-tissue implant 100 into a hard tissue, the hard tissue can immediately occupy all or part of the space corresponding to the slots 150. This can be accomplished, for example, by pressing the hard-tissue implant 100 into the hard tissue. Moreover, to the extent that the hard tissue does not, upon implantation, immediately occupy all of the space corresponding to slots 150, the hard tissue can eventually occupy all or part of the space corresponding to the slots 150 based on remodeling and/or growth of the hard tissue over time, e.g. during healing.

As shown in FIG. 8, FIG. 9, and FIG. 10, the pillars 140 define the slots 150 therebetween, i.e. the slots 150 are the spaces between the pillars 140. Accordingly, as shown in FIG. 10, the slots 150 have a slot height 440 as defined by the pillars 140, of, for example, 100 to 10,000 μm, 100 to 5,000 μm, 200 to 2,500 μm, 300 to 1,000 μm, 400 to 600 μm, 450 to 550 μm, or 500 μm. As shown in FIG. 12A to FIG. 12E, the slots 150 have a slot width 152 as measured along the shortest distance between adjacent pillars 140 of, for example, 100 to 10,000 μm, 100 to 7,500 μm, 100 to 3,000 μm, 150 to 1,000 μm, 175 to 450 μm, 190 to 410 μm, 190 to 210 μm, or 390 to 410 μm. The slots 150 have a volume 710 corresponding to the volume of the space between the pillars 140.

Considering now the at least one support member 180 in more detail, as shown in FIG. 1, the at least one support member 180 also is for contacting the hard tissue. The hard tissue can be a hard tissue as discussed above.

The at least one support member 180 is positioned on the face 120 of the hard-tissue implant 100 among the pillars 140, extending distally from the face 120, and having a transverse area 182 greater than the transverse area 510 of any of the pillars 140.

The at least one support member 180 can have a distal end 184. The at least one support member 180 can have a support member height 186, i.e. the height of the at least one support member 180 from the face 120 of the hard-tissue implant 100 to the distal end 184 of the at least one support member 180, that is less than, the same as, or greater than the height 420 of one, many, or all of the pillars 140. The distal end 184 of the at least one support member 180 can include an opening, e.g. such that the hard-tissue implant 100 has a passage extending from the distal end 184 of the at least one support member 180, through the at least one support member 180, and through the bulk implant 110. Alternatively, the distal end 184 of the at least one support member 180 can lack an opening. The at least one support member 180 can have a support member axial surface 188. The support member axial surface 188 can be angled with respect to the face 120 of the hard-tissue implant 100, e.g. being generally transverse with respect to the face 120 of the hard-tissue implant 100, at an angle of 70° to 110°, 80° to 100°, or about 90°. The at least one support member 180 can be, for example, a rod, a tube, a raised rim surrounding a hole, a fin, or a keel, among other structures.

In accordance with some embodiments, the at least one support member 180 includes at least two support members 180. For example, the at least one support member 180 can include two, three, four, or more support members 180.

In accordance with some embodiments, the at least one support member 180 is integral to the bulk implant 110, i.e. the at least one support member 180 and the bulk implant 110 are made from the same starting material, rather than, for example, the at least one support member 180 being an add-on to the bulk implant 110. Like the bulk implant 110, the at least one support member 180 can be porous, e.g. including pores having diameters of, e.g. 1 to 900 μm, 100 to 800 μm, or 200 to 600 μm, or the at least one support member 180 can be non-porous.

In accordance with some embodiments, the support member axial surface 188 can include support member pillars 190 extending therefrom, e.g. support member pillars 190 like the pillars 140 described above, distributed across all or part of the support member axial surface 188. As will be appreciated, for hard-tissue implants 100 that include at least one support member 180 that includes a support member axial surface 188 that is angled with respect to the face 120 of the hard-tissue implant 100, and that further includes support member pillars 190 extending from the support member axial surface 188, then the support member pillars 190 extending from the support member axial surface 188 can be angled with respect to the pillars 140 extending from the face 120 of the hard-tissue implant 100.

Also in accordance with some embodiments, the support member axial surface 188 can lack pillars, e.g. all or part of the support member axial surface 188 can lack pillars. In accordance with these embodiments, the support member axial surface 188 can be, for example, a smooth surface, a rough surface, a flat surface, a curved surface, and/or an irregular surface, among others.

The hard-tissue implant 100 has a ratio of (i) the sum of the volumes 710 of the slots 150 to (ii) the sum of the volumes 520 of the pillars 140 and the volumes 710 of the slots 150, of, for example, 0.40:1 to 0.90:1, 0.51:1 to 0.90:1, 0.51:1 to 0.60:1, or 0.70:1 to 0.76:1. Without wishing to be bound by theory, it is believed that this ratio determines the approximate percentages of hard tissue and hard-tissue implant 100 that will occupy the interface following implantation of the hard-tissue implant 100, e.g. that upon pressing the implant 100 into the hard tissue, or upon remodeling and growth of the hard-tissue following implantation, that the hard tissue will occupy all or essentially all of the space corresponding to the slots 150 of the hard-tissue implant 100.

Figure 13:
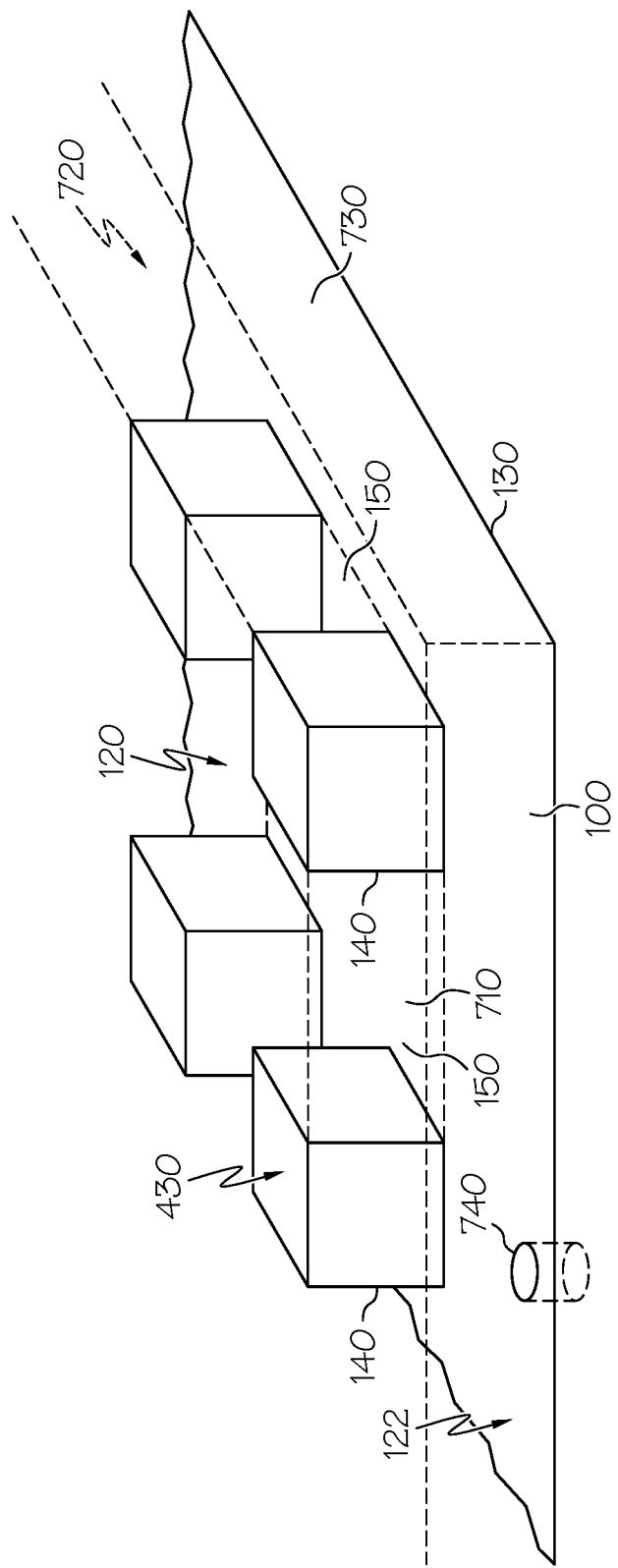
FIG. 13 is a schematic perspective view of part of a portion of a hard-tissue implant including pillars.
Figure 14:
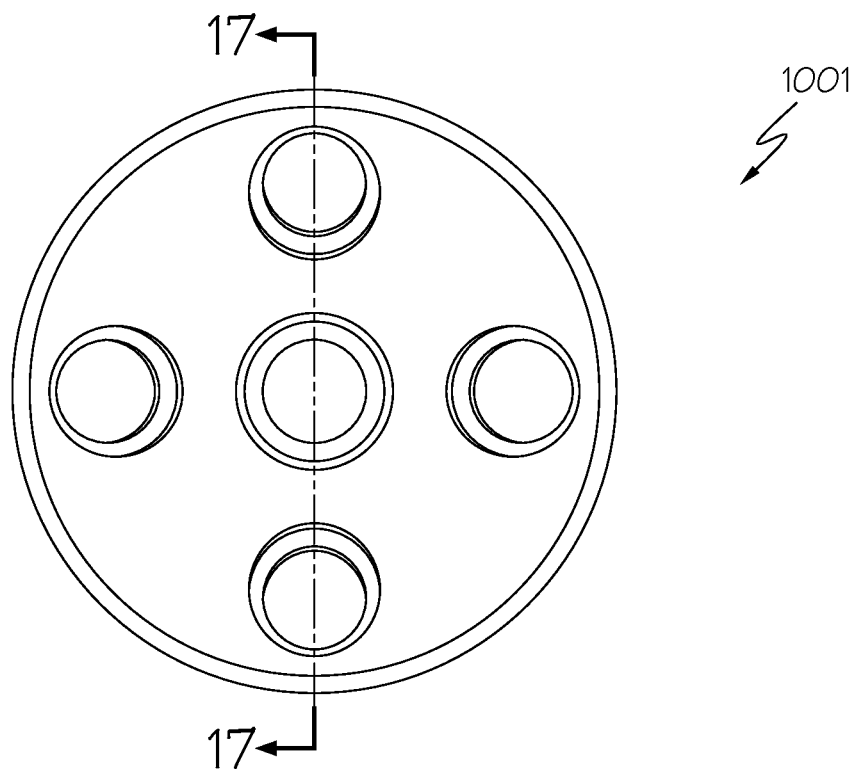
FIG. 14 is a top view of the glenoid implant for shoulder of FIG. 1.
Figure 15:
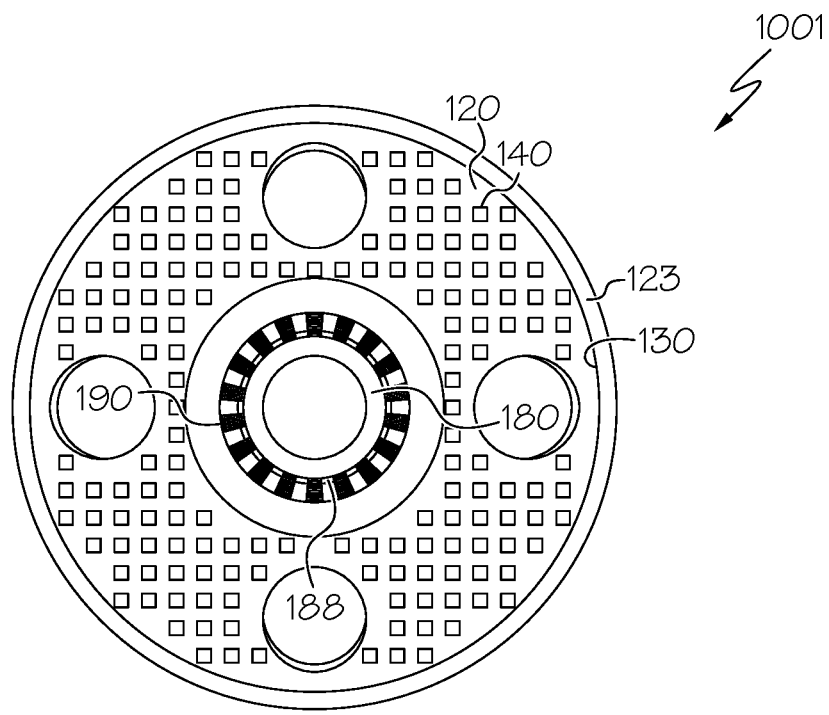
FIG. 15 is a bottom view of the glenoid implant for shoulder of FIG. 1.
Figure 16:
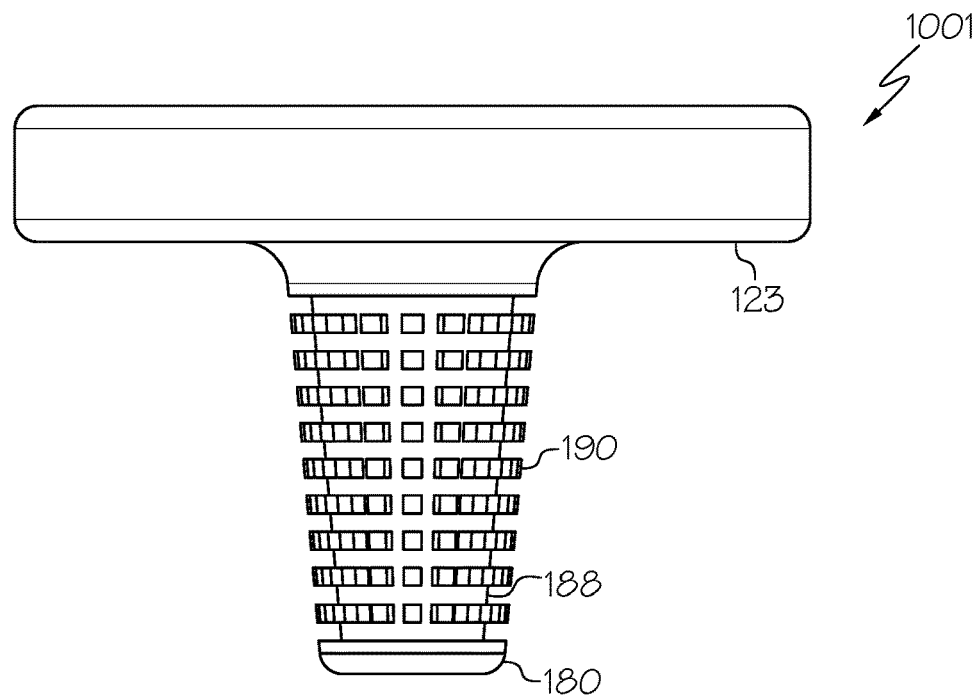
FIG. 16 is a side view of the glenoid implant for shoulder of FIG. 1.
Figure 17:
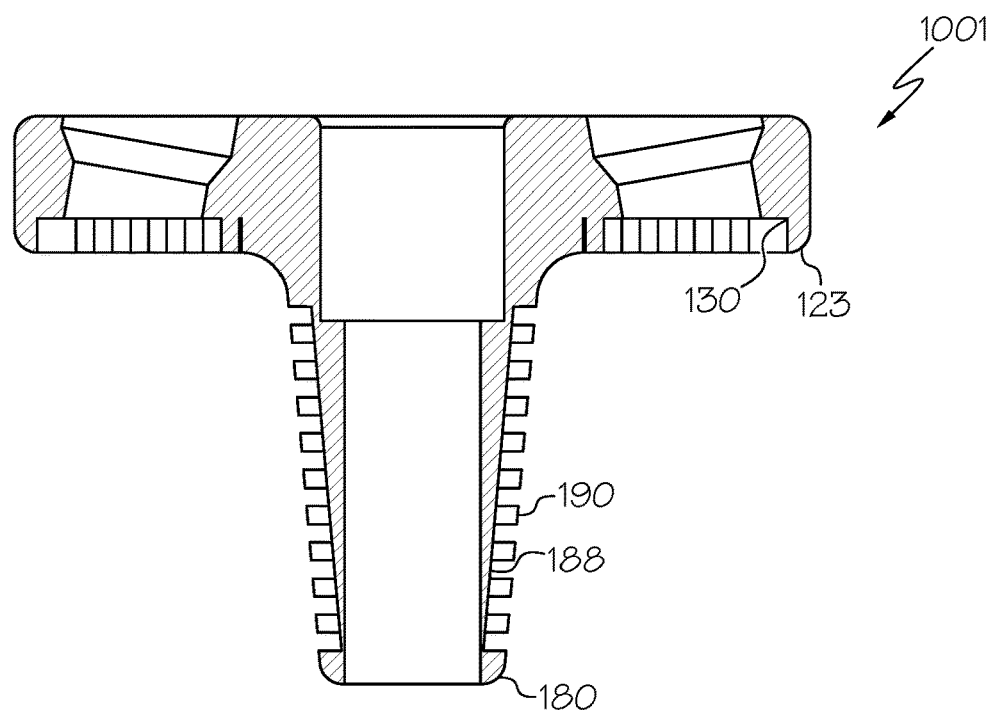
FIG. 17 is a sectional view of the glenoid implant for shoulder of FIG. 14.
Figure 18:
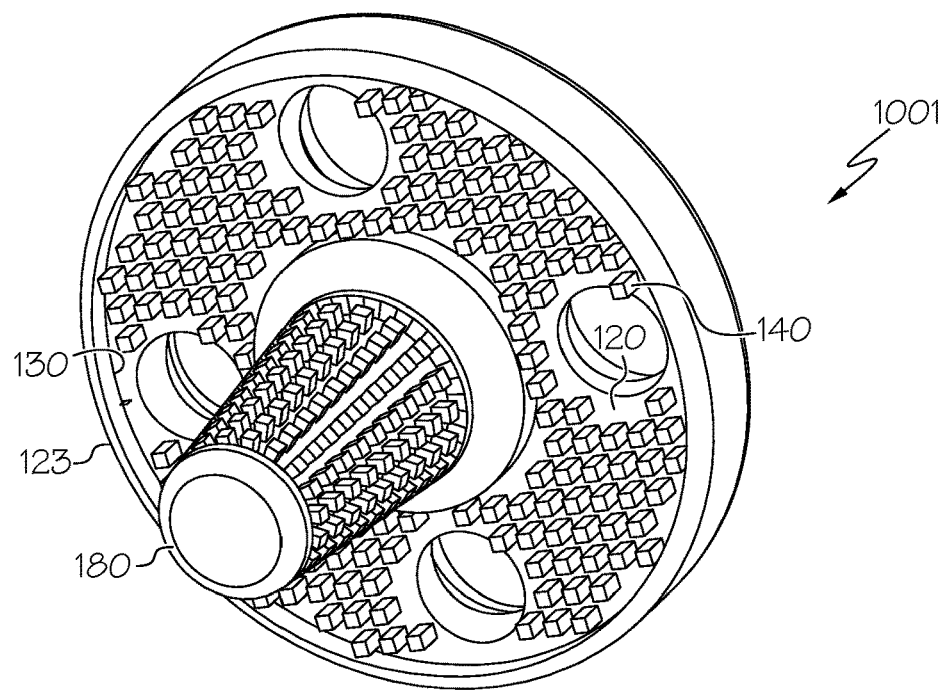
FIG. 18 is a bottom perspective view of the glenoid implant for shoulder of FIG. 1.
Figure 19:
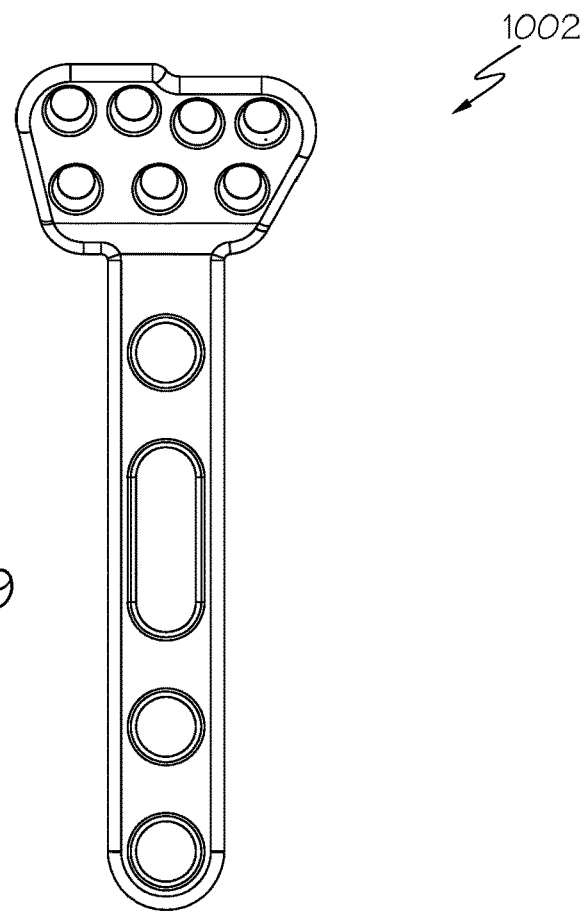
FIG. 19 is a top view of the distal radius plate implant for wrist of FIG. 2.
Figure 20:
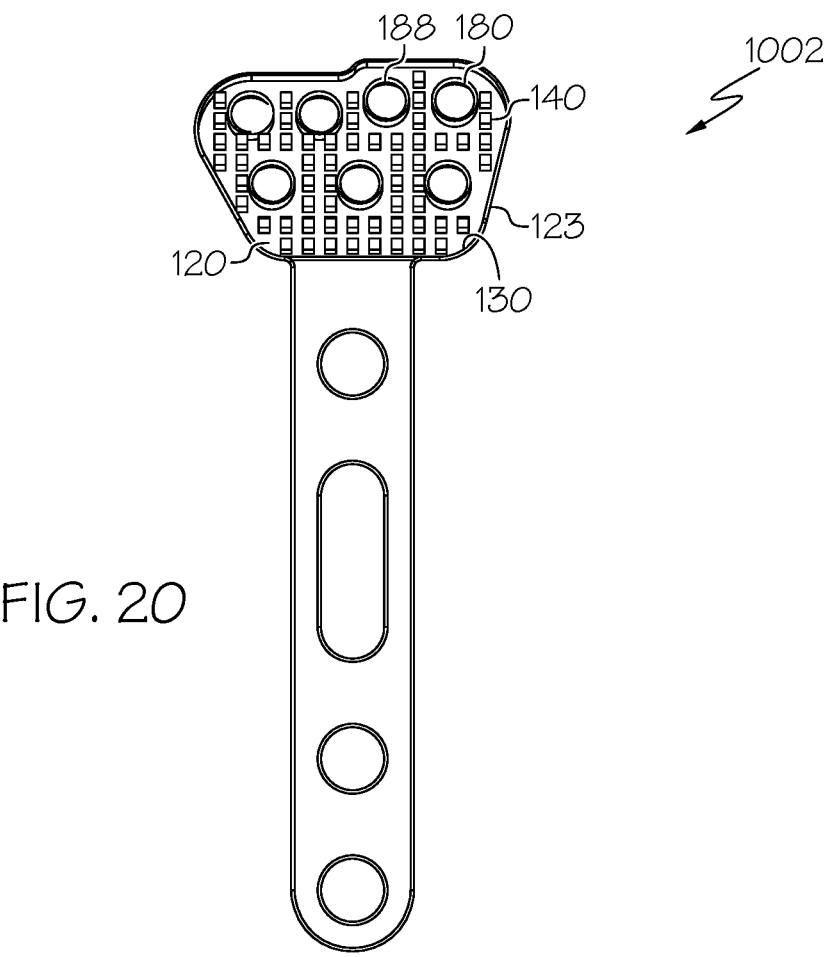
FIG. 20 is a bottom view of the distal radius plate implant for wrist of FIG. 2.
Figure 21:
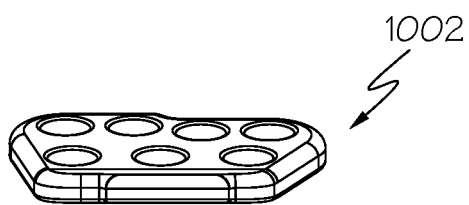
FIG. 21 is a first side view of the distal radius plate implant for wrist of FIG. 2.
Figure 22:
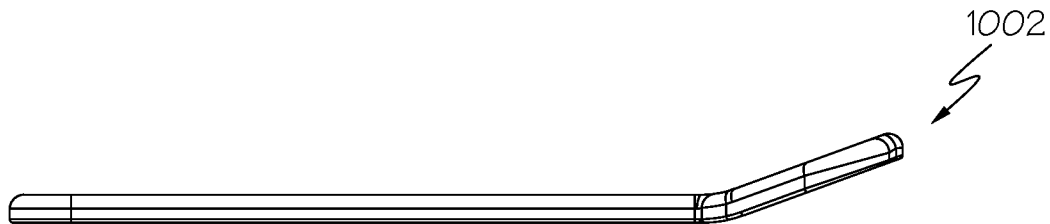
FIG. 22 is a second side view of the distal radius plate implant for wrist of FIG. 2.
Figure 23:
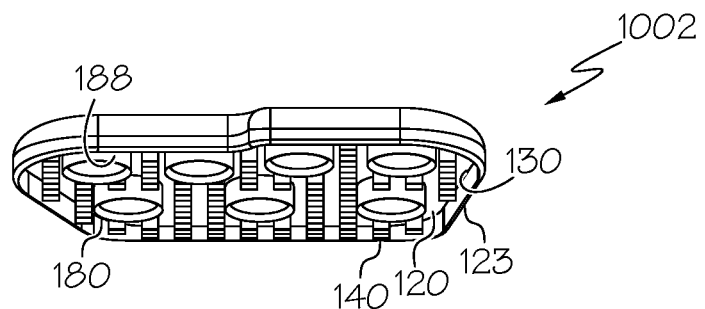
FIG. 23 is a third side view of the distal radius plate implant for wrist of FIG. 2.
Figure 24:
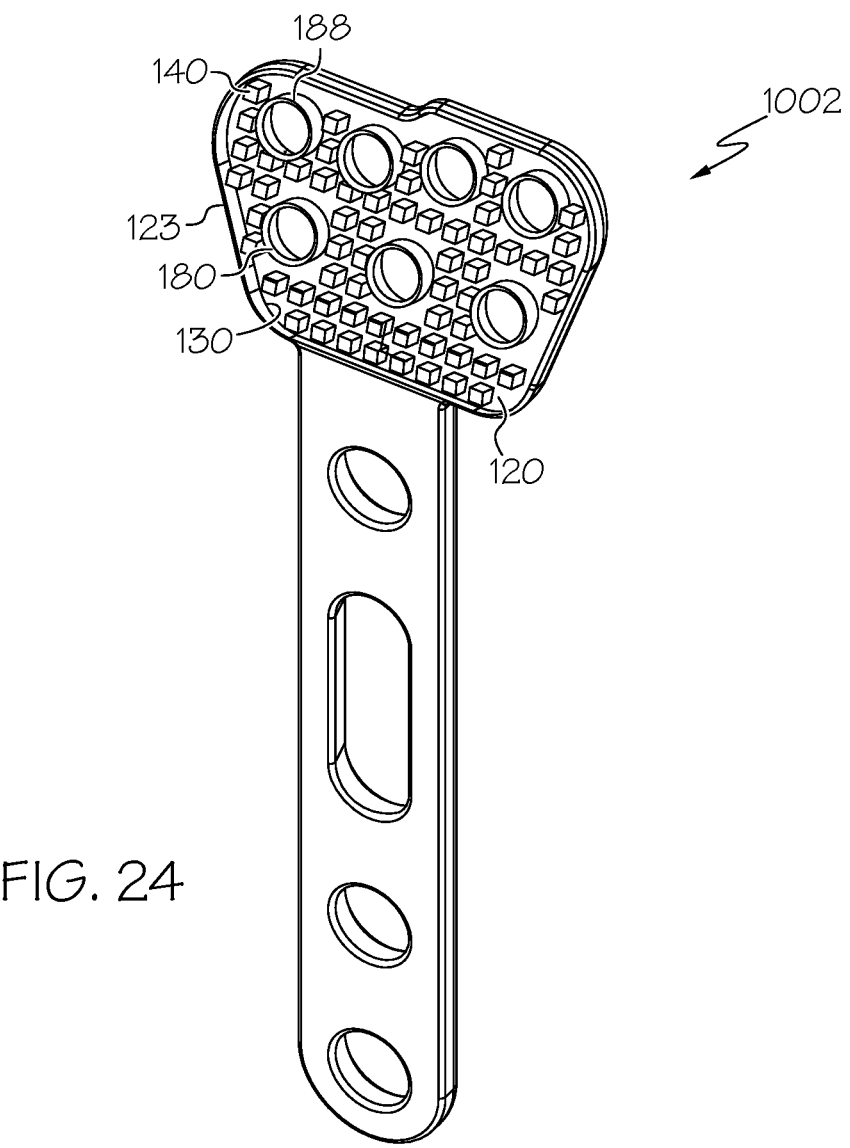
FIG. 24 is a bottom perspective view of the distal radius plate implant for wrist of FIG. 2.
Figure 25:
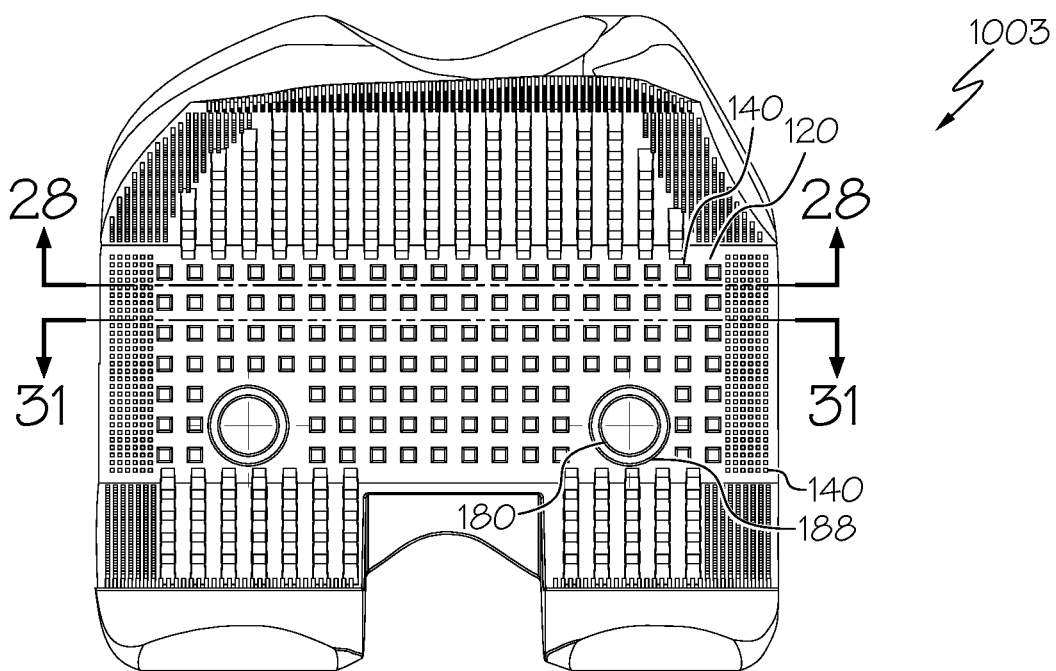
FIG. 25 is a top view of the femoral capture implant for knee of FIG. 3.
Figure 26:
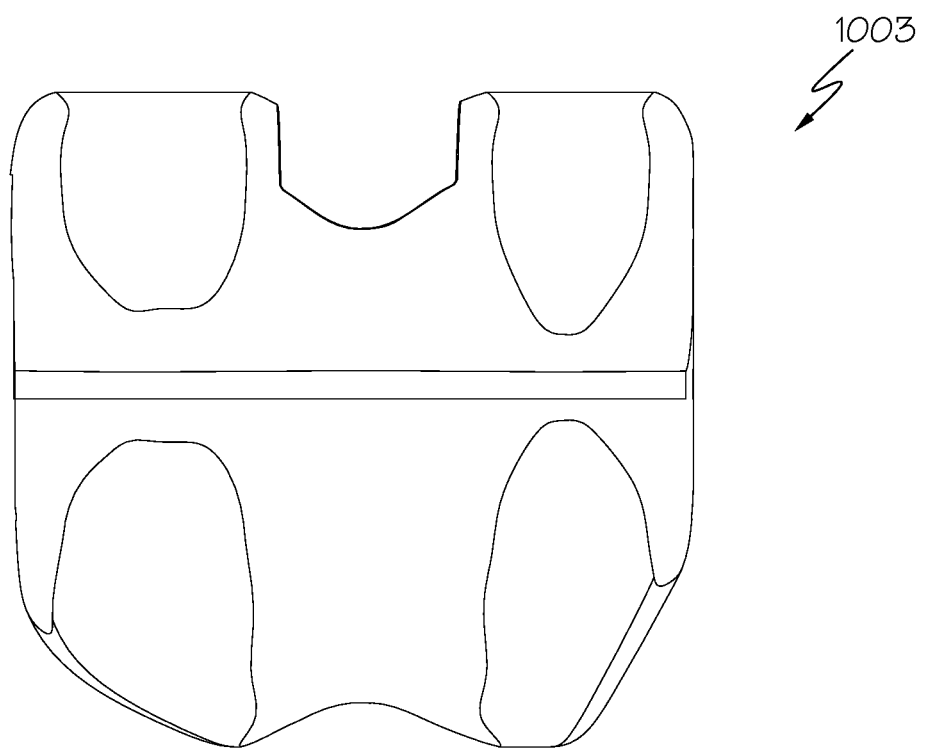
FIG. 26 is a bottom view of the femoral capture implant for knee of FIG. 3.
Figure 27:
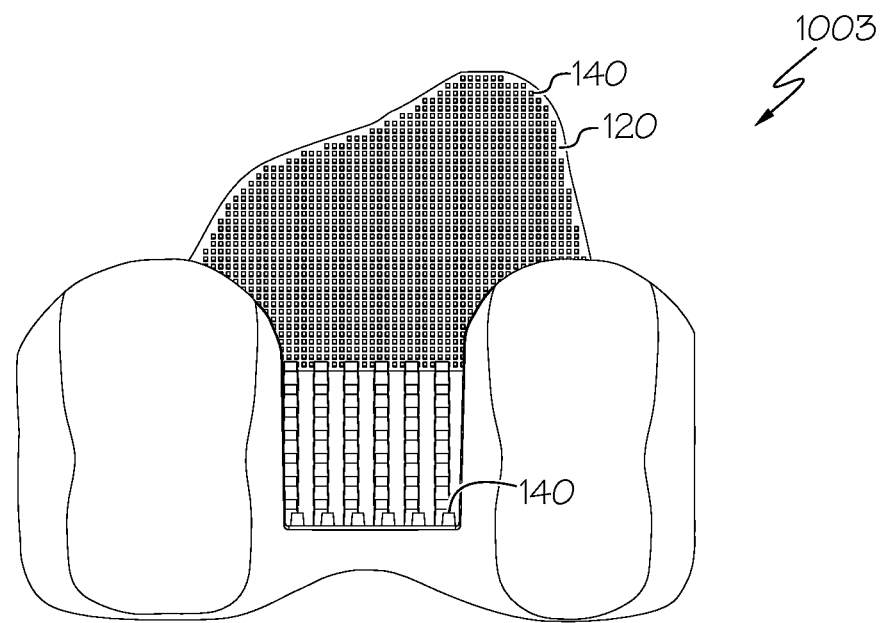
FIG. 27 is a first side view of the femoral capture implant for knee of FIG. 3.
Figure 28:
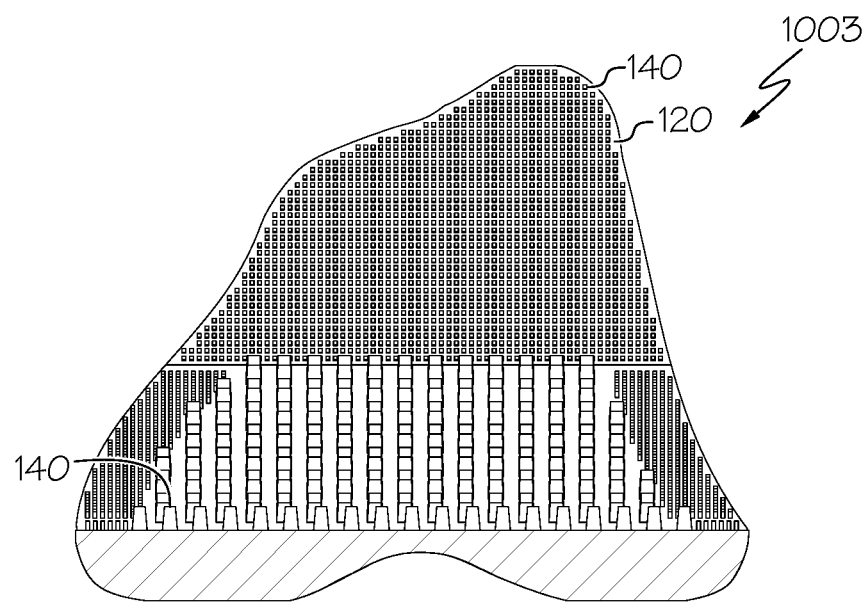
FIG. 28 is a sectional view of the femoral capture implant for knee of FIG. 25.
Figure 29:
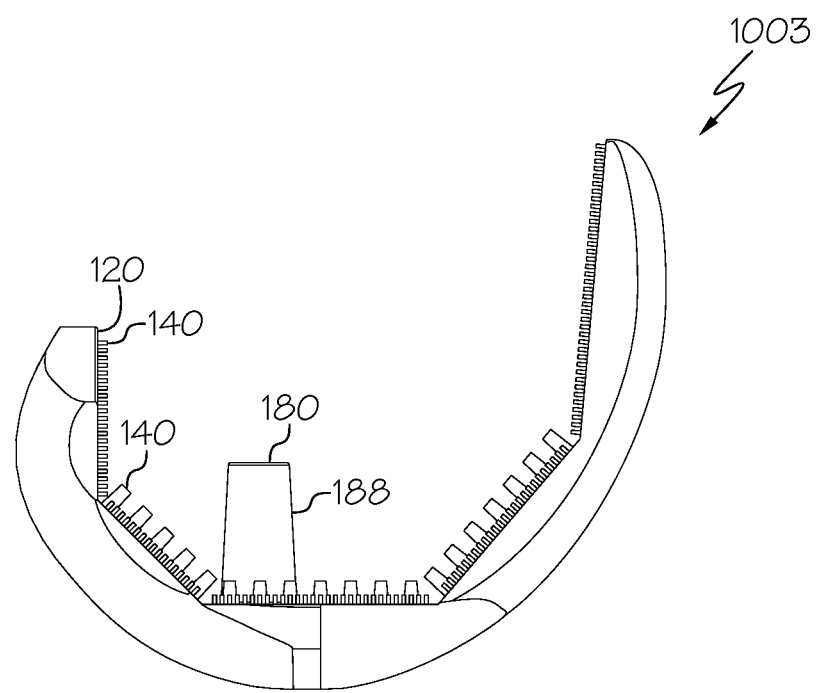
FIG. 29 is a second side view of the femoral capture implant for knee of FIG. 3.
Figure 30:
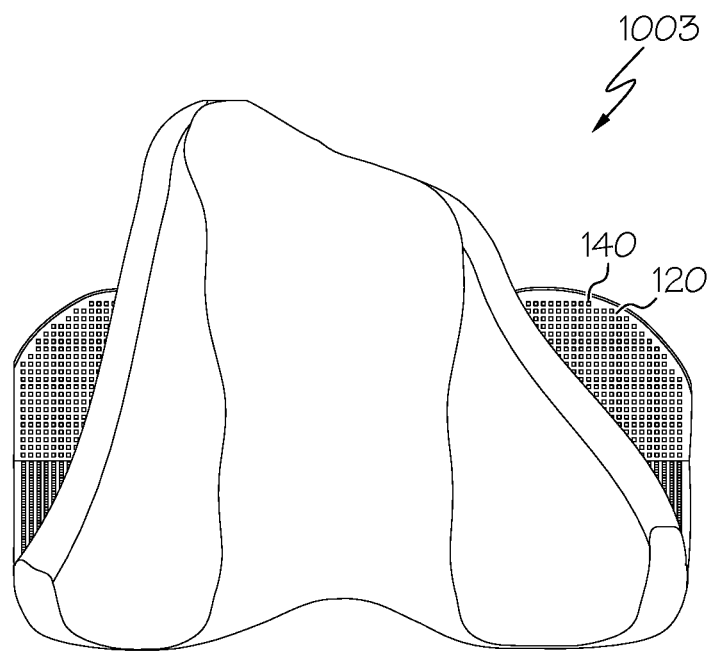
FIG. 30 is a third side view of the femoral capture implant for knee of FIG. 3.
Figure 31:
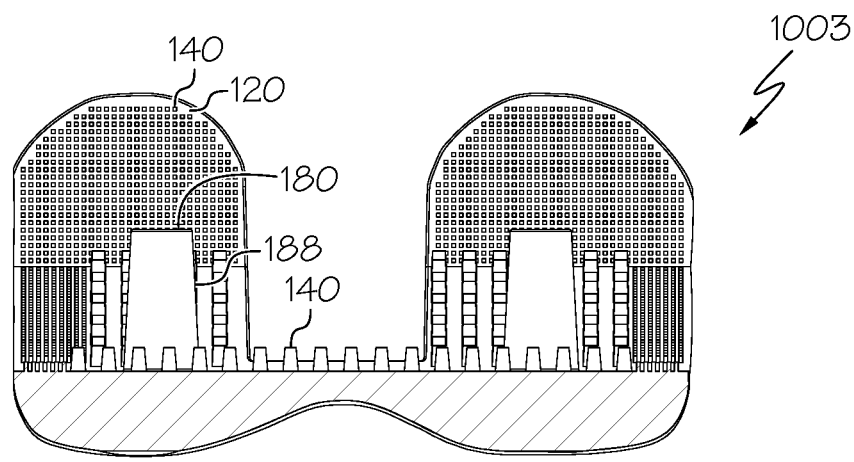
FIG. 31 is a sectional view of the femoral capture implant for knee of FIG. 25.
Figure 32:
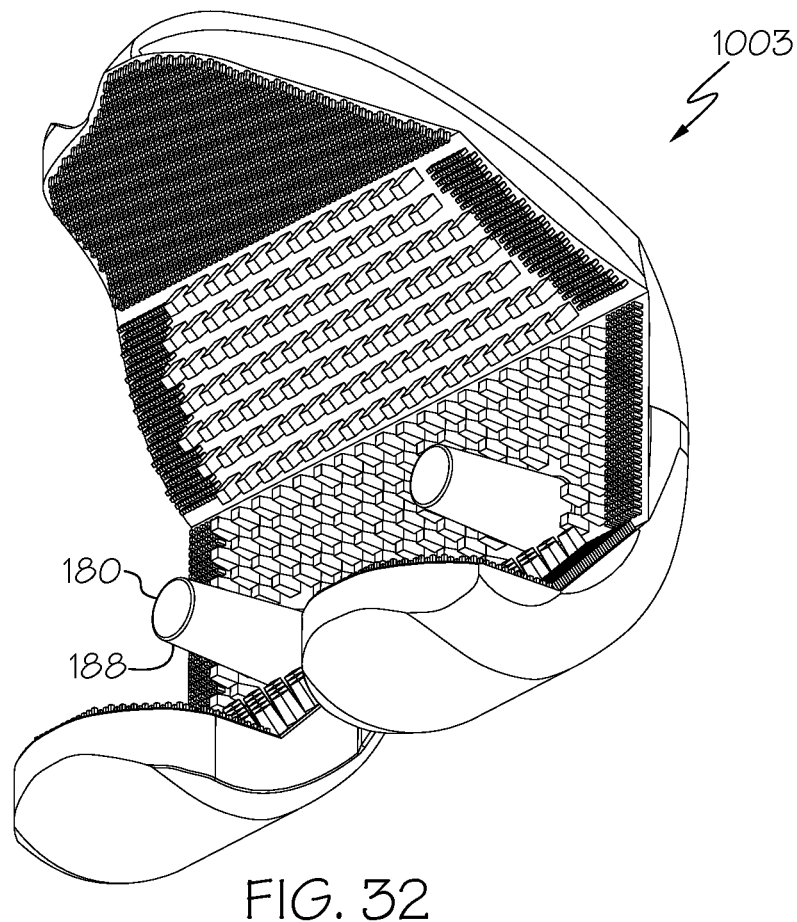
FIG. 32 is a top perspective view of the femoral capture implant for knee of FIG. 3.
Figure 33:
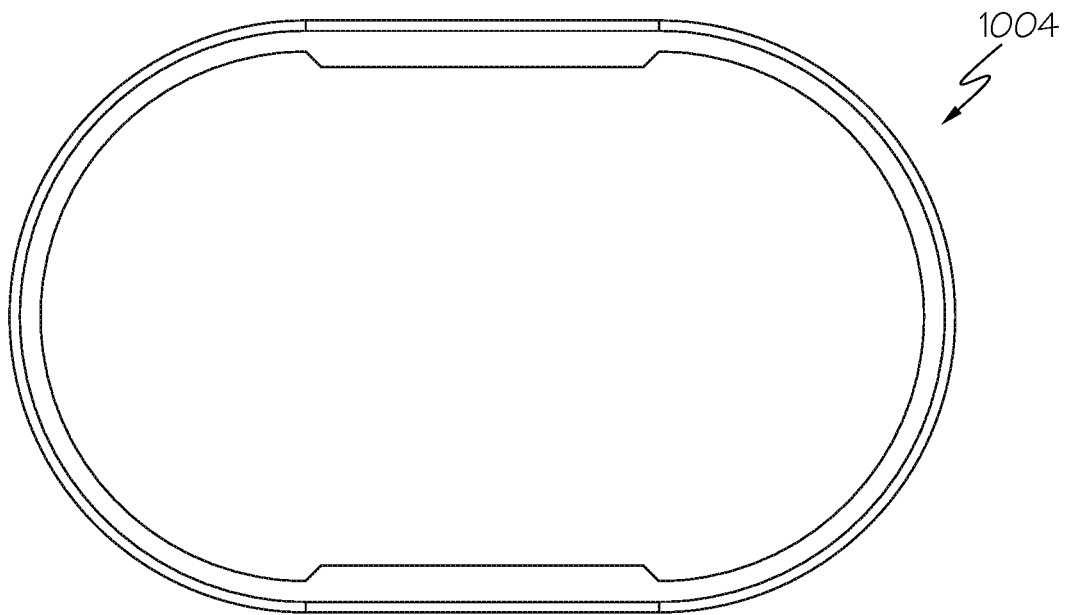
FIG. 33 is a top view of the tibial implant for knee of FIG. 4.
Figure 34:
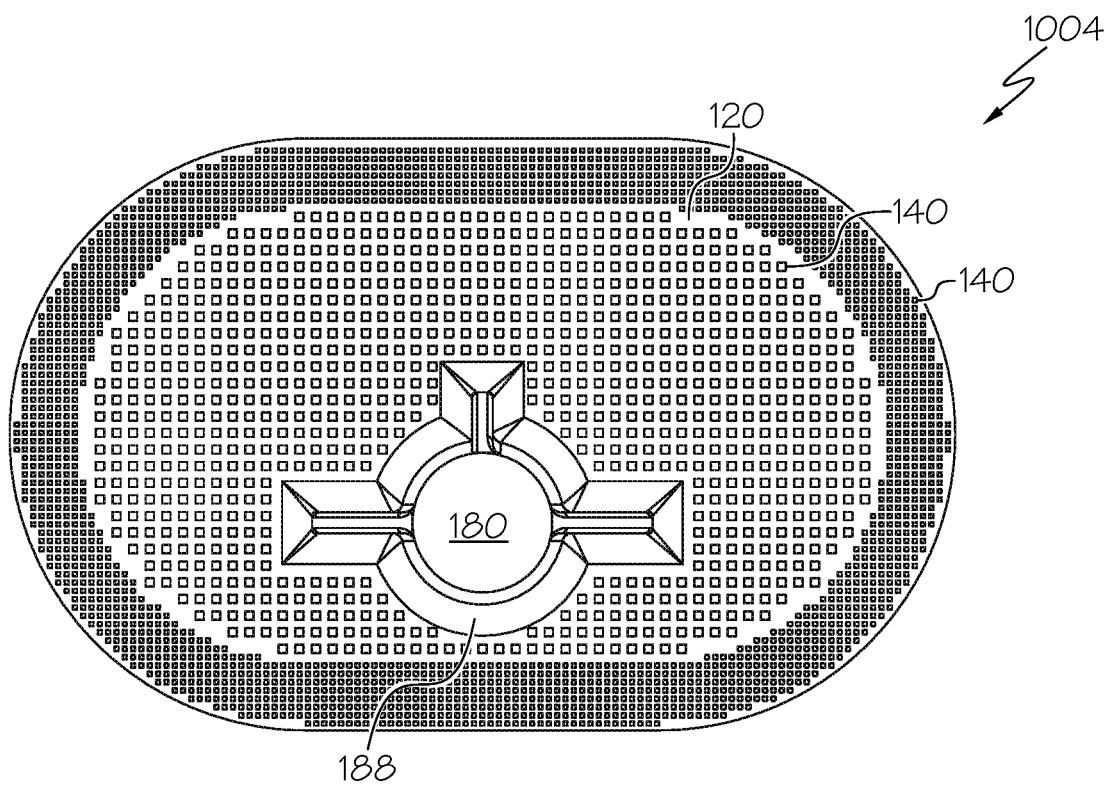
FIG. 34 is a bottom view of the tibial implant for knee of FIG. 4.
Figure 35:
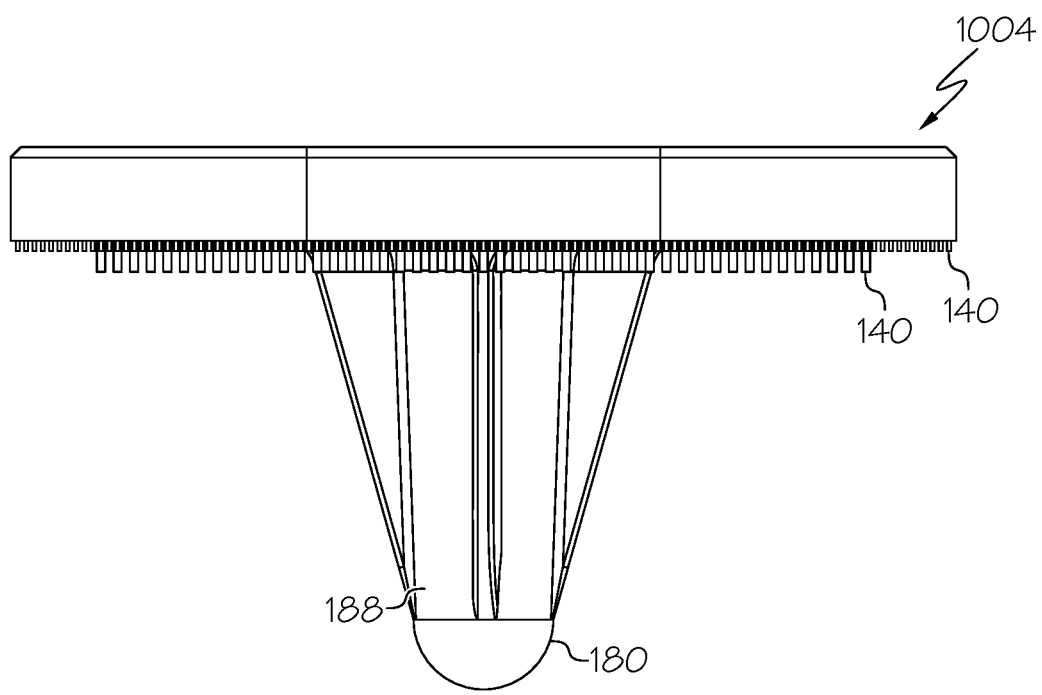
FIG. 35 is a first side view of the tibial implant for knee of FIG. 4.
Figure 36:
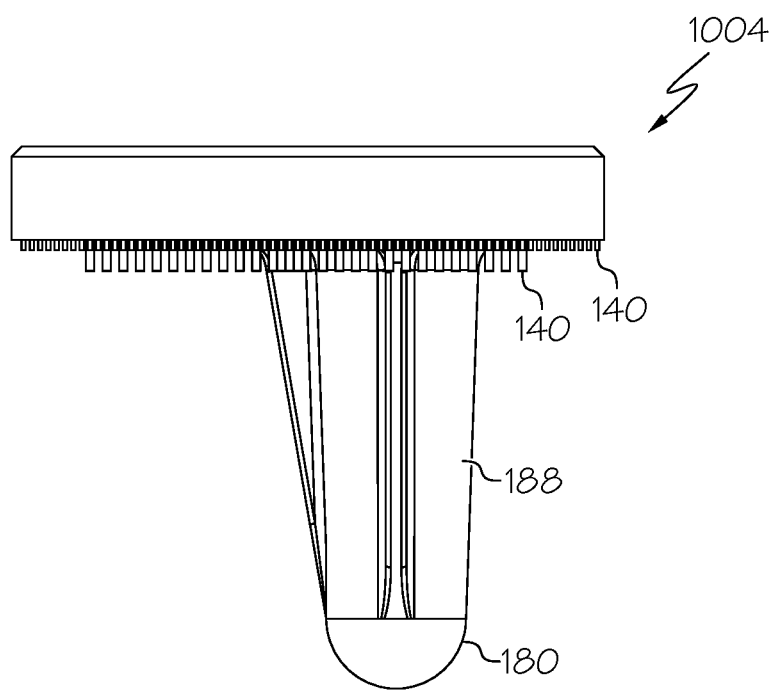
FIG. 36 is a second side view of the tibial implant for knee of FIG. 4.
Figure 37:
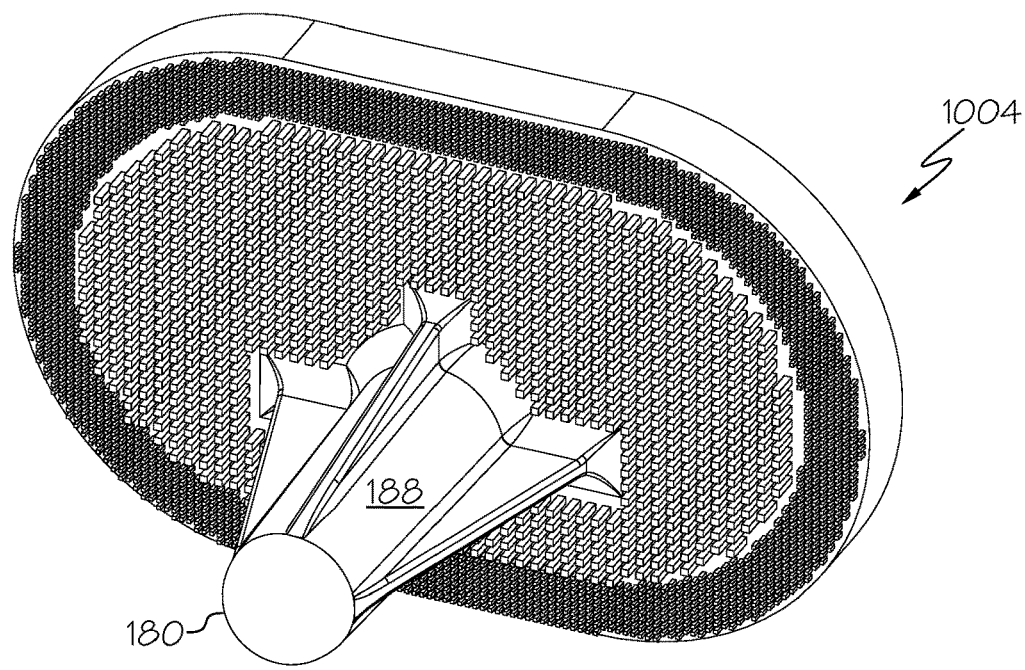
FIG. 37 is a bottom perspective view of the tibial implant for knee of FIG. 4.
Figure 38:
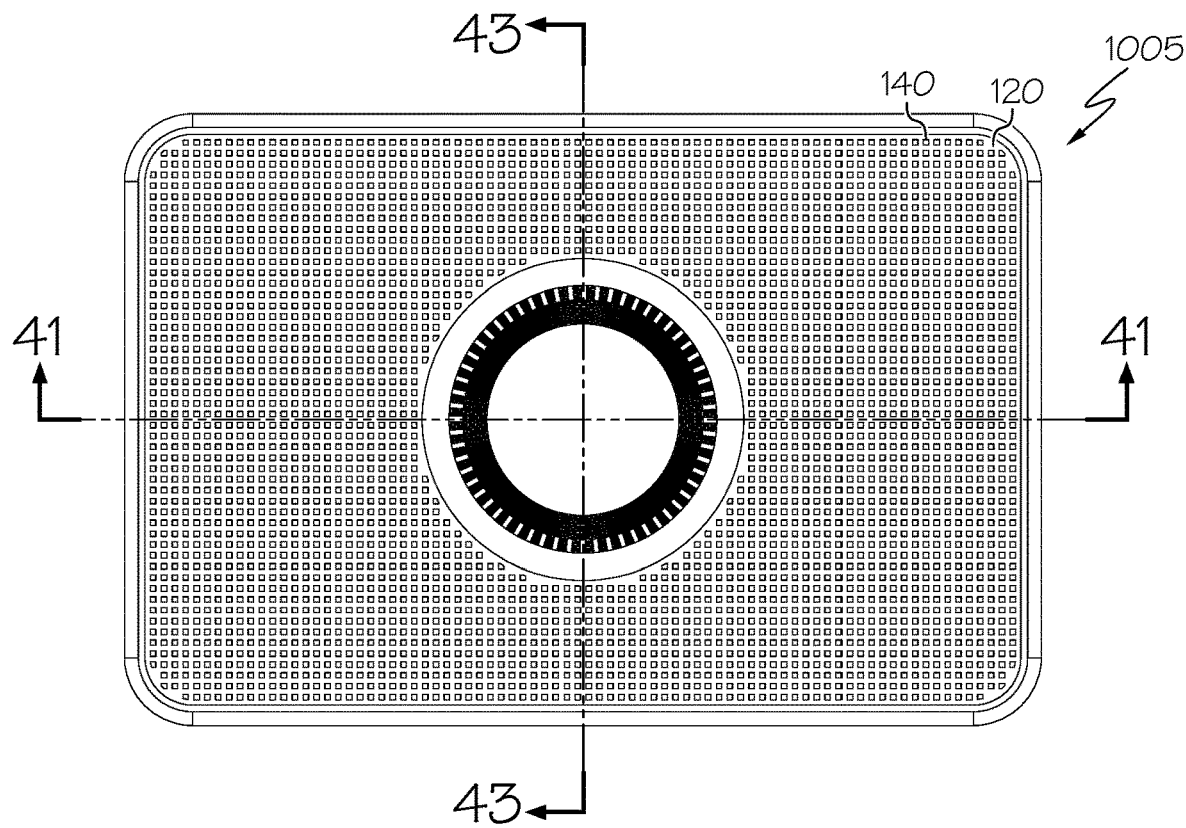
FIG. 38 is a top view of the tibial implant for ankle of FIG. 5.
Figure 39:
FIG. 39 is a bottom view of the tibial implant for ankle of FIG. 5.
Figure 40:
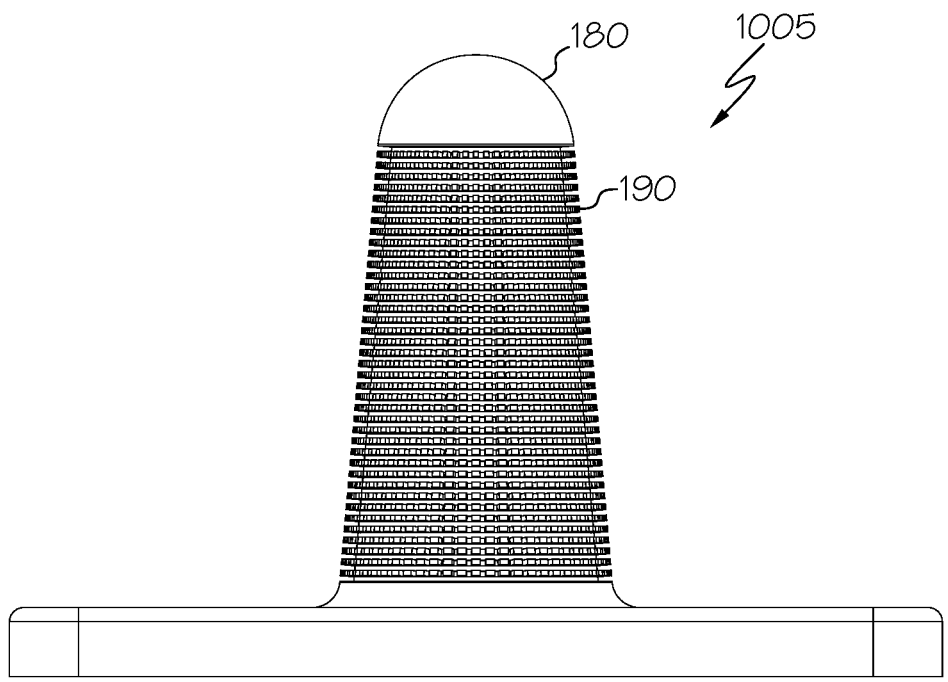
FIG. 40 is a first side view of the tibial implant for ankle of FIG. 5.
Figure 41:
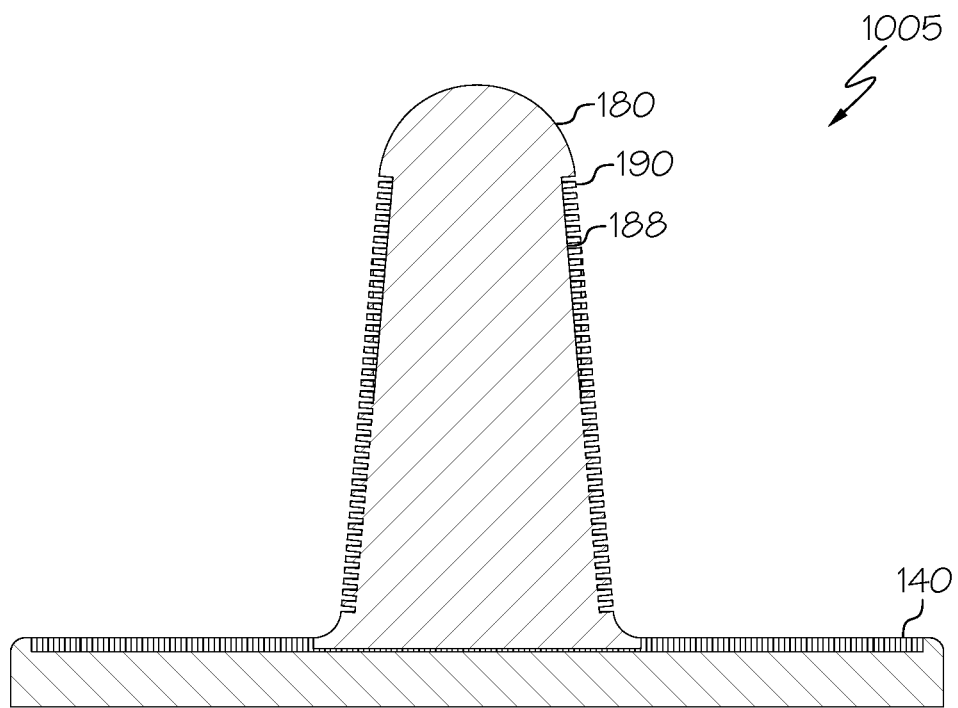
FIG. 41 is a sectional view of the tibial implant for ankle of FIG. 38.
Figure 42:
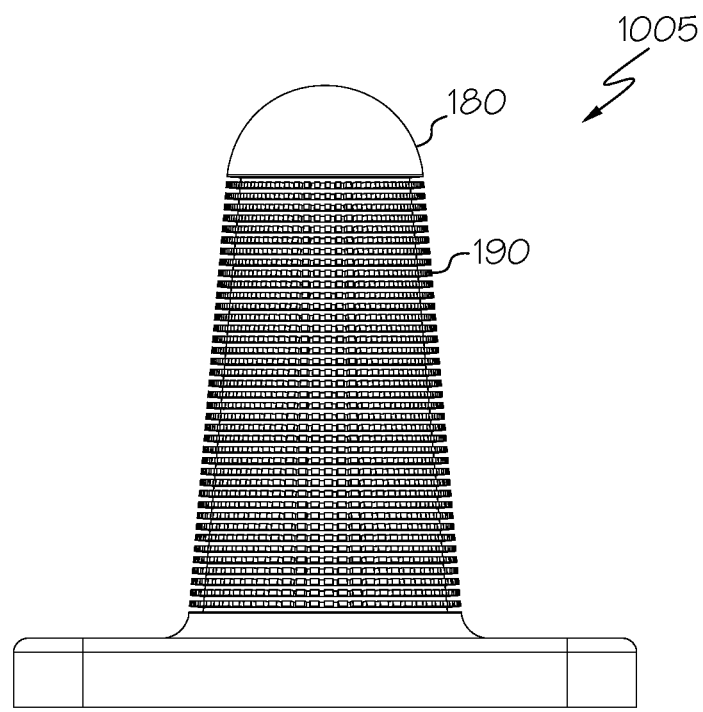
FIG. 42 is a second side view of the tibial implant for ankle of FIG. 5.
Figure 43:
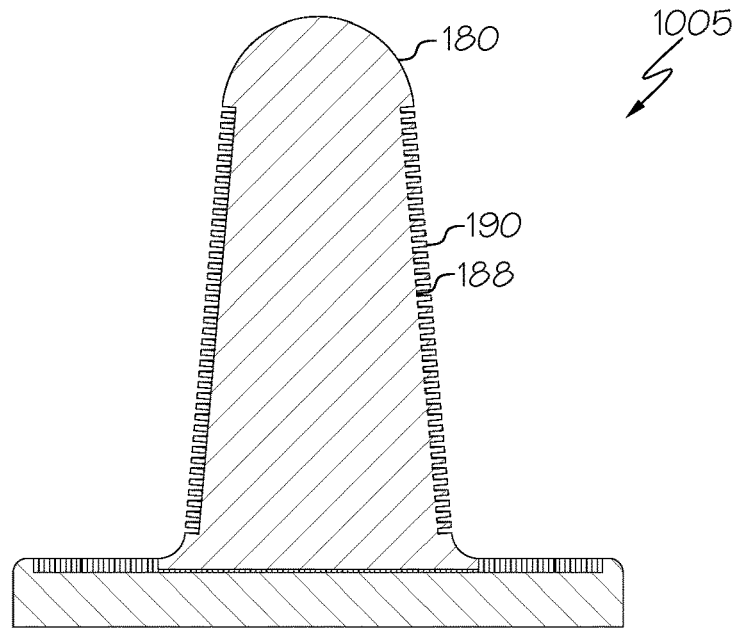
FIG. 43 is a sectional view of the tibial implant for ankle of FIG. 38.
Figure 44:
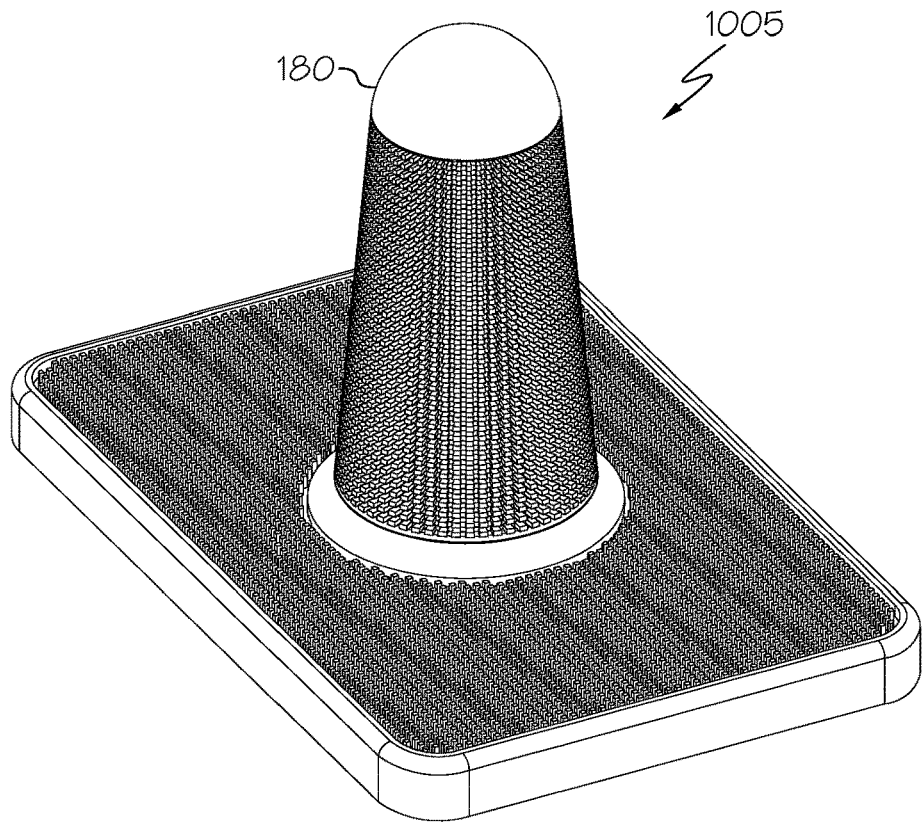
FIG. 44 is a top perspective view of the tibial implant for ankle of FIG. 5.
Figure 45:
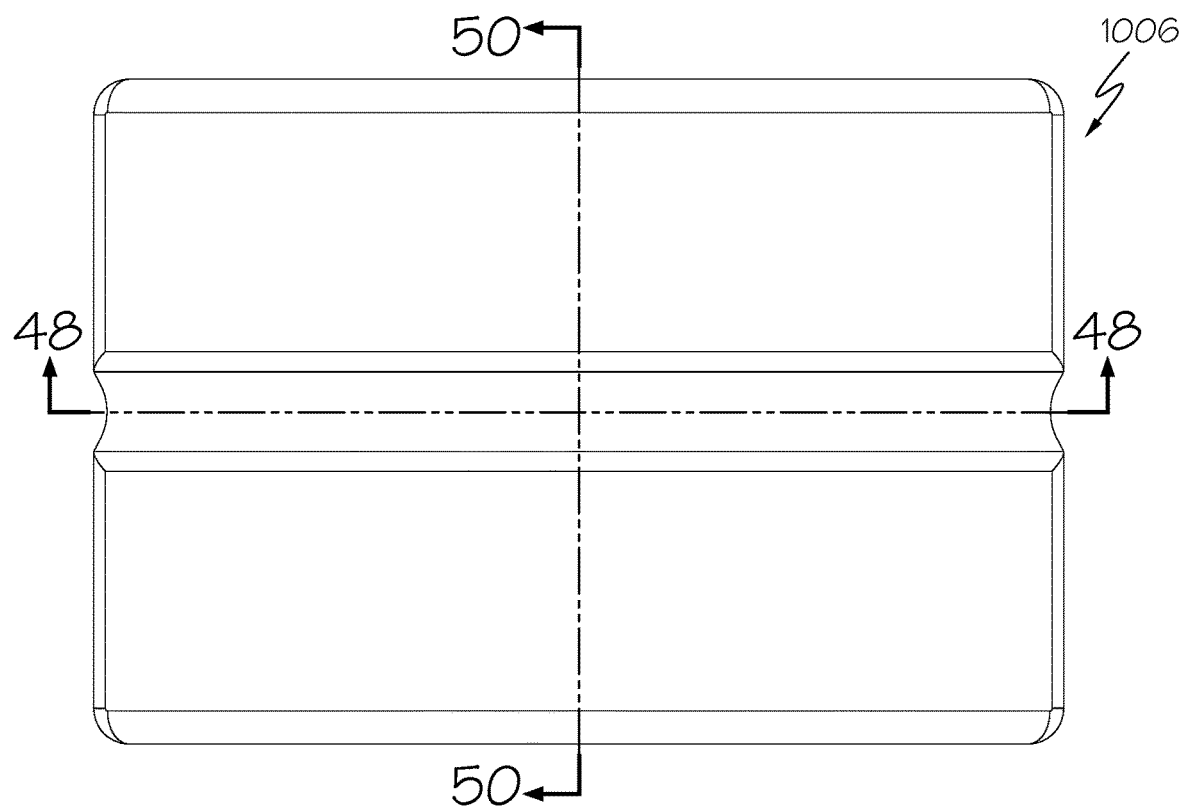
FIG. 45 is a top view of the talar implant for ankle of FIG. 6.
Figure 46:
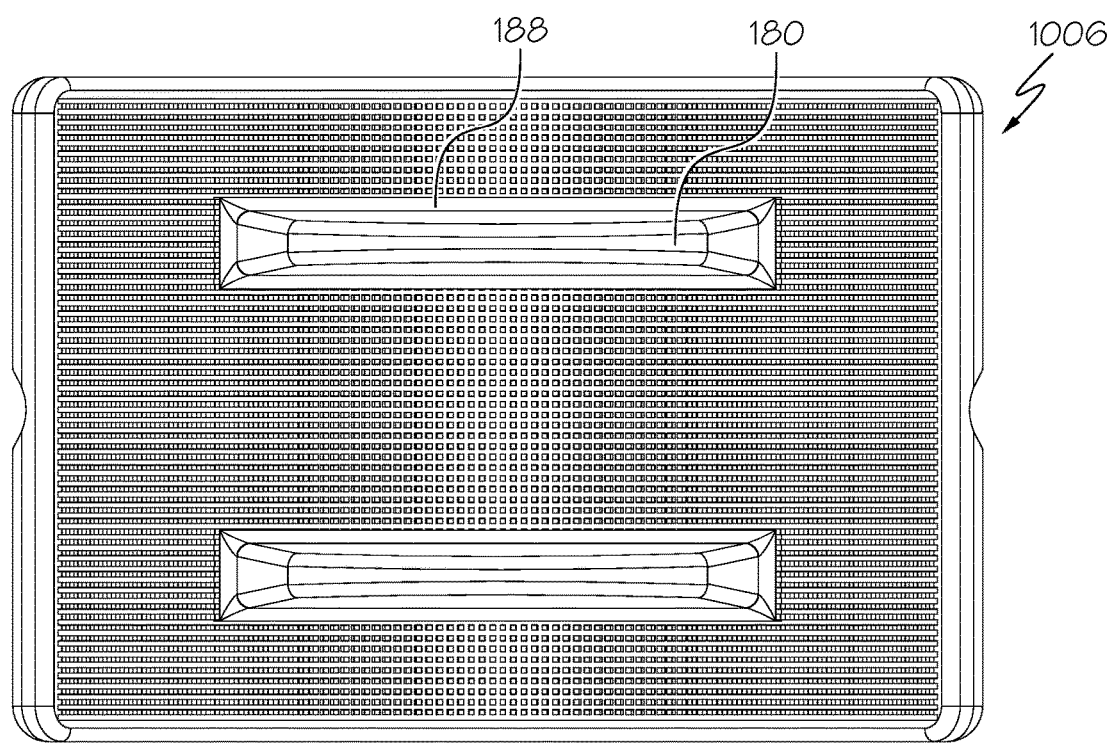
FIG. 46 is a bottom view of the talar implant for ankle of FIG. 6.
Figure 47:
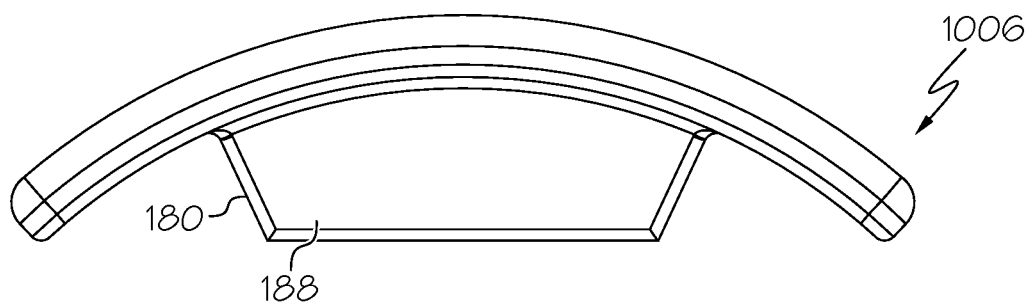
FIG. 47 is a first side view of the talar implant for ankle of FIG. 6.
Figure 48:
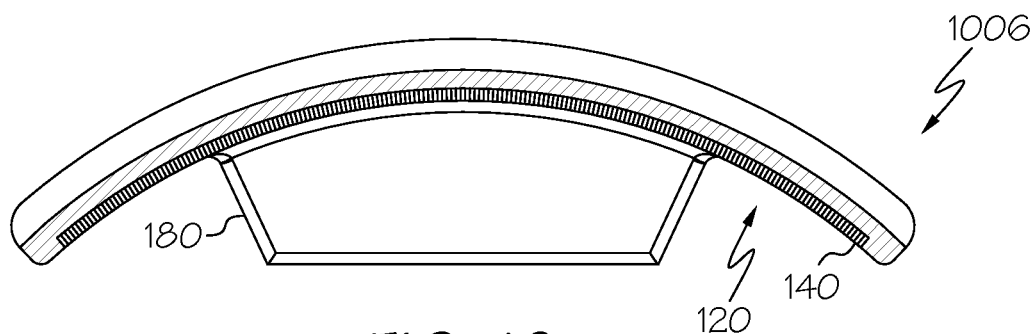
FIG. 48 is a sectional view of the talar implant for ankle of FIG. 45.
Figure 49:
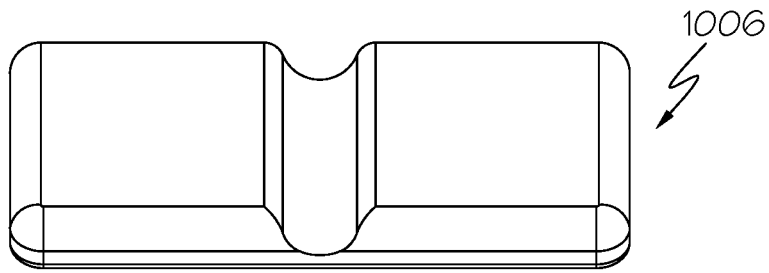
FIG. 49 is a second side view of the talar implant for ankle of FIG. 6.
Figure 50:
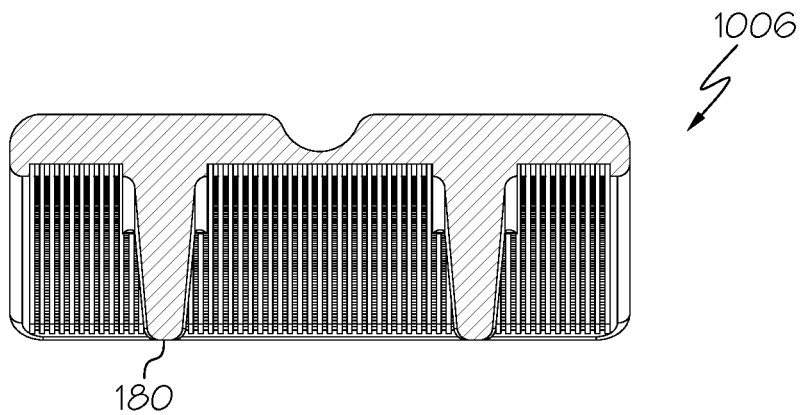
FIG. 50 is a sectional view of the talar implant for ankle of FIG. 45.
Figure 51:
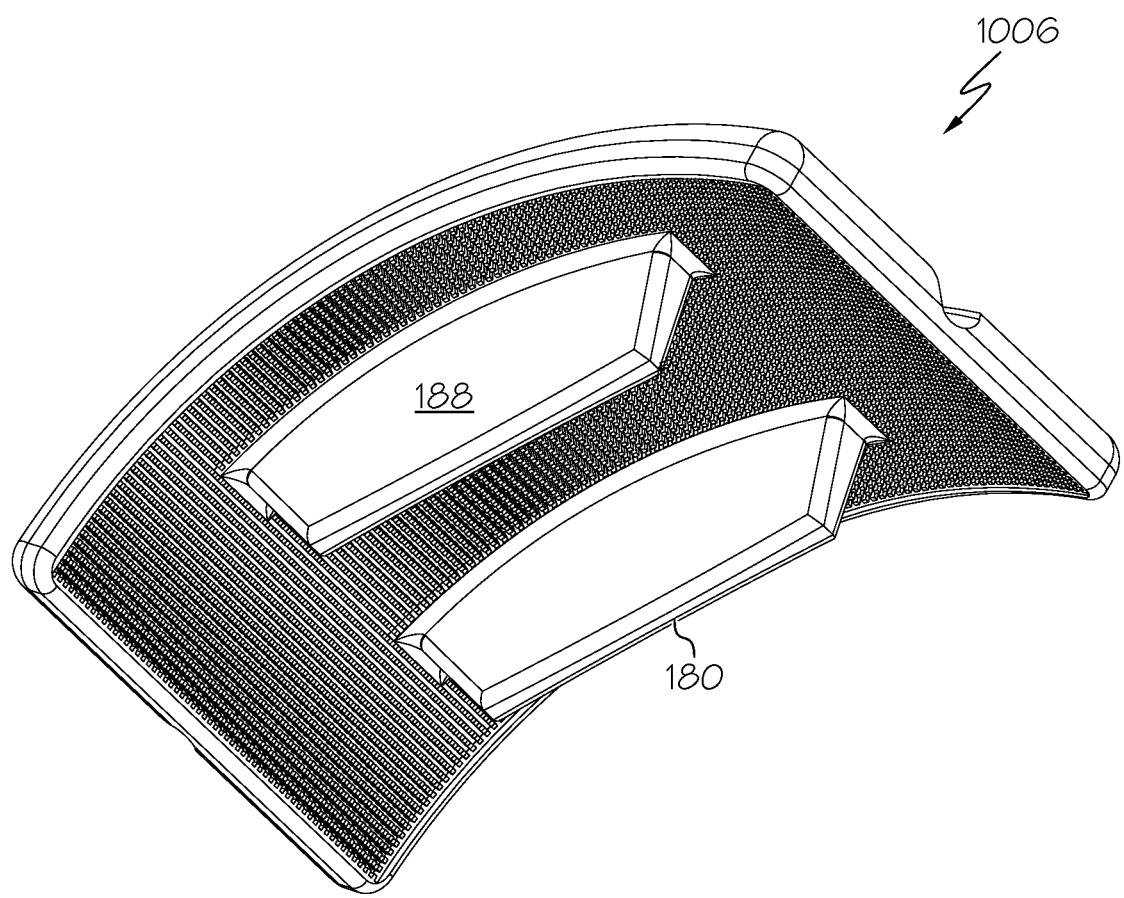
FIG. 51 is a bottom perspective view of the talar implant for ankle of FIG. 6.

More specifically, as shown in FIG. 13, the interface includes (i) the pillars 140, (ii) the slots 150 of the hard-tissue implant 100, which have a volume 710 and which, upon or following implantation, become occupied by hard tissue, (iii) any additional space between the face 120 of the implant 100 and a plane 720 defined by the distal ends 430 of the pillars 140, e.g. the space between the peripheral border 122 of the face 120 that is not occupied by pillars 140 and the plane 720, which has a volume 730 and which also becomes occupied by hard tissue (thus excluding volume occupied by the support member 180), and (iv) any pores 740 on the face 120 or the pillars 140, which, depending on their size, may also become occupied by hard tissue.

Accordingly, for example, a ratio of the sum of (i) the volumes 710 of the slots 150 to (ii) the sum of the volumes 520 of the pillars 140 and the volumes 710 of the slots 150 of 0.40:1 would, following implantation of a hard-tissue implant 100 and subsequent remodeling and growth of hard tissue, wherein the implant 100 includes an edge 130 and for which pillars 140 are located at the edge 130, result in an interface that includes by volume 40% hard tissue and 60% hard-tissue implant 100, and more particularly 60% pillars 140 of the hard-tissue implant 100. Similarly, a ratio of (i) the sum of the volumes 710 of the slots 150 to (ii) the sum of the volumes 520 of the pillars 140 and the volumes 710 of the slots 150 of 0.40:1 would, following implantation of a hard-tissue implant 100 and subsequent remodeling and growth of hard tissue, wherein the implant 100 includes an edge 130 and for which no pillars 140 are located at the edge 130, result in an interface that includes by volume more than 40% hard tissue and less than 60% hard-tissue implant 100, with the percentage of hard tissue increasing, and the percentage of hard-tissue implant 100 decreasing, with increasing distance between the peripheral-most pillars 140 and slots 150 and the edge 130 of the hard-tissue implant 100. By way of further examples, ratios of 0.51:1, 0.60:1, 0.70:1, 0.76:1, and 0.90:1, would result in interfaces that include, by volume, 51% hard tissue and 49% hard-tissue implant 100, 60% hard tissue and 40% hard-tissue implant 100, 70% hard tissue and 30% hard-tissue implant 100, 76% hard tissue and 24% hard-tissue implant 100, and 90% hard tissue and 10% hard-tissue implant, respectively, for a hard-tissue implant 100 wherein the implant 100 includes an edge 130 and for which pillars 140 are located at the edge 130. Moreover, the percentage of hard tissue would increase, and the percentage of hard-tissue implant 100 would decrease, with increasing distance between the peripheral-most pillars 140 and slots 150 and the edge 130 of the hard-tissue implant 100. It is further believed that by achieving an interface that is at least 40% hard tissue, but that has a sufficient amount of the hard-tissue implant 100 to provide support and to keep the implant 100 from migrating, that the interface will exhibit properties similar to those of the bulk hard tissue adjacent to the interface, e.g. high resilience to load. It also is believed that by including at least one support member 180 among the pillars 140 that support for the hard-tissue implant 100 will be improved.

Considering example embodiments of the hard-tissue implant 100 in more detail, in one example embodiment, the Young's modulus of the hard-tissue implant 100 is 18 to 25 GPa and the ratio of (i) the sum of the volumes 710 of the slots 150 to (ii) the sum of the volumes 520 of the pillars 140 and the volumes 710 of the slots 150 is 0.51:1 to 0.60:1. In another example embodiment, the Young's modulus of the hard-tissue implant 100 is 100 to 110 GPa and the ratio of (i) the sum of the volumes 710 of the slots 150 to (ii) the sum of the volumes 520 of the pillars 140 and the volumes 710 of the slots 150 is 0.70:1 to 0.76:1. In another example embodiment, the hard-tissue implant 100 is made of implantable-grade polyetheretherketone with filler, the transverse area 510 of each pillar 140 is (350 μm×350 μm) to (450 μm×450 μm), the pillar height 420 of each pillar 140 is 400 to 600 μm, the slot width 152 of each slot 150 is 190 to 210 μm, and the ratio of (i) the sum of the volumes 710 of the slots 150 to (ii) the sum of the volumes 520 of the pillars 140 and the volumes 710 of the slots 150 is 0.85:1 to 1.6:1. In another example embodiment, the hard-tissue implant 100 is made of implantable-grade polyetheretherketone with filler, the transverse area 510 of each pillar 140 is (395 μm×395 μm) to (405 μm×405 μm), the pillar height 420 of each pillar 140 is 490 to 510 μm, the slot width 152 of each slot 150 is 190 to 210 μm, and the ratio of (i) the sum of the volumes 710 of (ii) the slots 150 to the sum of the volumes 520 of the pillars 140 and volumes 710 of the slots 150 is 0.92:1 to 1.4:1. In another example embodiment, the hard-tissue implant 100 is made of titanium, the transverse area 510 of each pillar 140 is (350 μm×350 μm) to (450 μm×450 μm), the pillar height 420 of each pillar 140 is 400 to 600 μm, the slot width 152 of each slot 150 is 390 to 410 μm, and the ratio of (i) the sum of the volumes 710 of the slots 150 to (ii) the sum of the volumes 520 of the pillars 140 and the volumes 710 of the slots 150 is 2.2:1 to 3.7:1. In another example embodiment, the hard-tissue implant 100 is made of titanium, the transverse area 510 of each pillar 140 is (395 μm×395 μm) to (405 μm×405 μm), the pillar height 420 of each pillar 140 is 490 to 510 μm, the slot width 152 of each slot 150 is 390 to 410 μm, and the ratio of (i) the sum of the volumes 710 of the slots 150 to (ii) the sum of the volumes 520 of the pillars 140 and the volumes 710 of the slots 150 is 2.4:1 to 3.5:1.

With reference to FIG. 1, the glenoid implant for shoulder 1001 exemplifies a hard-tissue implant 100 in which the support member 180 has (1) a support member height 186 that is greater than the height 420 of all of the pillars 140, (2) a support member axial surface 188 that is angled with respect to the face 120 of the hard-tissue implant 100, e.g. being generally transverse with respect to the face 120 of the hard-tissue implant 100, and (3) a support member axial surface 188 that includes support member pillars 190 extending therefrom, distributed across all or part of the support member axial surface 188. The glenoid implant for shoulder 1001 also exemplifies a hard-tissue implant 100 in which the edge 130 includes a raised wall 123 that extends above the face 120, such that the face 120 is recessed with respect to the raised wall 123, and (2) the pillar height 420 is the same as a height of the raised wall 123.

Figure 2:
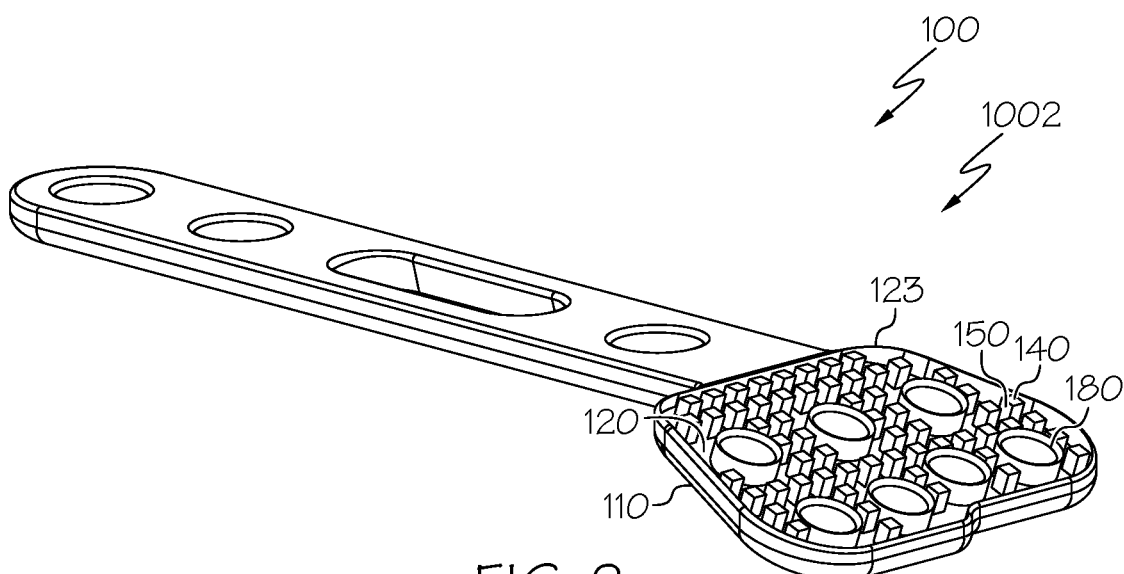
FIG. 2 is a perspective view of a hard-tissue implant corresponding to a distal radius plate implant for wrist.

With reference to FIG. 2, the distal radius plate implant for wrist 1002 exemplifies a hard-tissue implant 100 in which the support member 180 has (1) a support member height 186 that is the approximately the same as the height 420 of all of the pillars 140, (2) a support member axial surface 188 that is angled with respect to the face 120 of the hard-tissue implant 100, e.g. being generally transverse with respect to the face 120 of the hard-tissue implant 100, and (3) a support member axial surface 188 that lacks pillars. The distal radius plate implant for wrist 1002 also exemplifies a hard-tissue implant 100 including more than one support member 180. In this case each support member 180 corresponds to a raised rim surrounding a hole, for screws. The distal radius plate implant for wrist 1002 also exemplifies a hard-tissue implant 100 in which the edge 130 includes a raised wall 123 that extends above the face 120, such that the face 120 is recessed with respect to the raised wall 123, and (2) the pillar height 420 is the same as a height of the raised wall 123.

With reference to FIG. 3, the femoral capture implant for knee 1003 exemplifies a hard-tissue implant 100 in which the support member 180 has (1) a support member height 186 that is greater than the height 420 of all of the pillars 140, (2) a support member axial surface 188 that is angled with respect to the face 120 of the hard-tissue implant 100, e.g. being generally transverse with respect to the face 120 of the hard-tissue implant 100, and (3) a support member axial surface 188 that lacks pillars. The femoral capture implant for knee 1003 also exemplifies a hard-tissue implant 100 in which one or more pillars 140 have dimensions that differ from those of other pillars 140, such that the pillar transverse areas 510 and/or pillar heights 420, and thus volumes, of the one or more pillars 140 differ from those of the other pillars 140. The femoral capture implant for knee 1003 also exemplifies a hard-tissue implant 100 in which the one or more pillars 140 are distributed peripherally with respect to the face 120 and are intended for insertion into cortical bone, and the other pillars 140 are distributed centrally with respect to the face 120 and are intended for insertion into cancellous bone.

Figure 4:
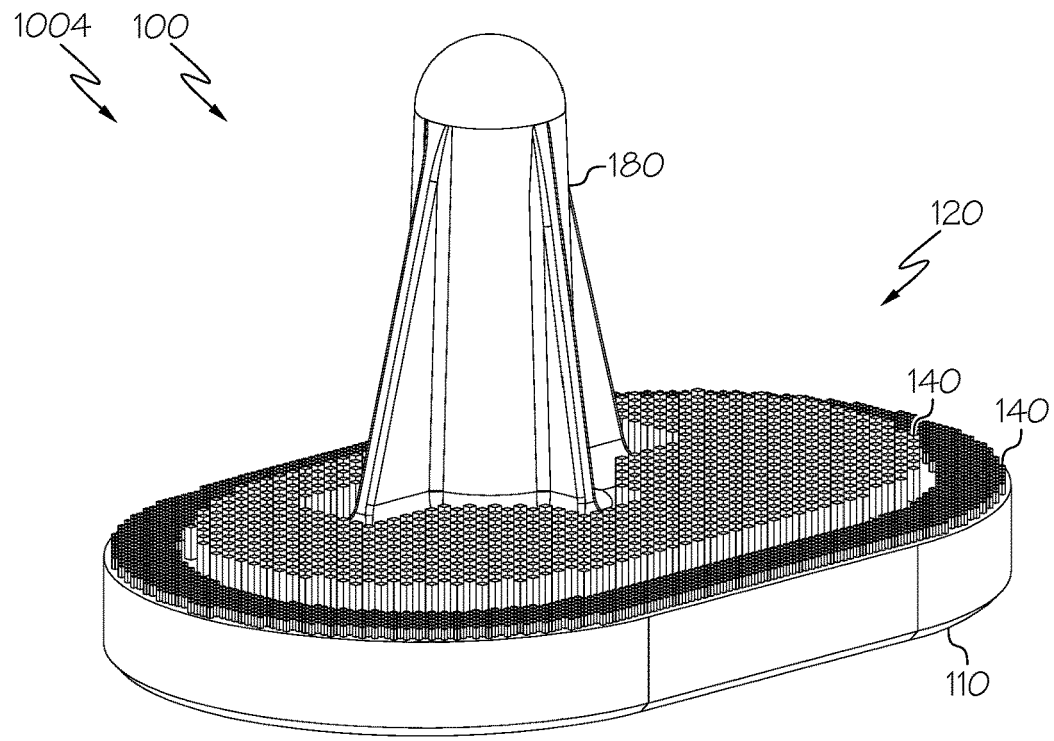
FIG. 4 is a perspective view of a hard-tissue implant corresponding to a tibial implant for knee.

With reference to FIG. 4, the tibial implant for knee 1004 exemplifies a hard-tissue implant 100 in which the support member 180 has (1) a support member height 186 that is greater than the height 420 of all of the pillars 140, (2) a support member axial surface 188 that is angled with respect to the face 120 of the hard-tissue implant 100, e.g. being generally transverse with respect to the face 120 of the hard-tissue implant 100, and (3) a support member axial surface 188 that lacks pillars. The tibial implant for knee 1004 also exemplifies a hard-tissue implant 100 in which one or more pillars 140 have dimensions that differ from those of other pillars 140, such that the pillar transverse areas 510 and/or pillar heights 420, and thus volumes, of the one or more pillars 140 differ from those of the other pillars 140. The tibial implant for knee 1004 also exemplifies a hard-tissue implant 100 in which the one or more pillars 140 are distributed peripherally with respect to the face 120 and are intended for insertion into cortical bone, and the other pillars 140 are distributed centrally with respect to the face 120 and are intended for insertion into cancellous bone.

Figure 5:
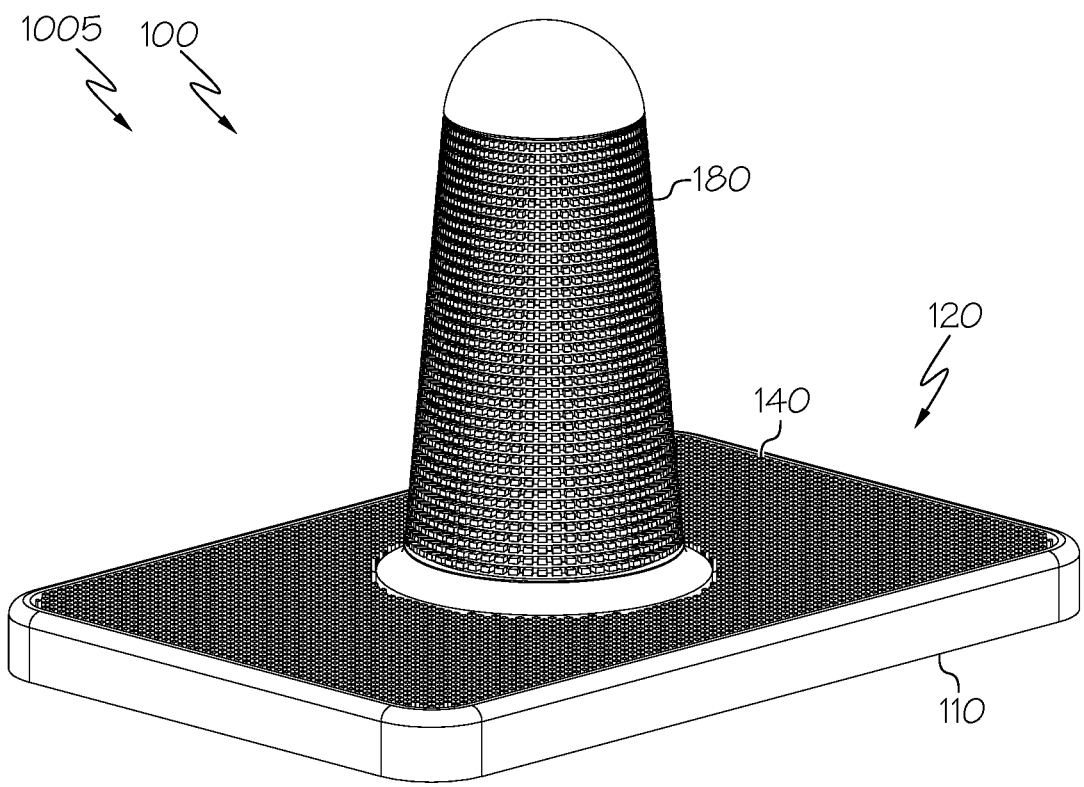
FIG. 5 is a perspective view of a hard-tissue implant corresponding to a tibial implant for ankle.

With reference to FIG. 5, the tibial implant for ankle 1005 exemplifies a hard-tissue implant 100 in which the support member 180 has (1) a support member height 186 that is greater than the height 420 of all of the pillars 140, (2) a support member axial surface 188 that is angled with respect to the face 120 of the hard-tissue implant 100, e.g. being generally transverse with respect to the face 120 of the hard-tissue implant 100, and (3) a support member axial surface 188 that includes support member pillars 190 extending therefrom, distributed across all or part of the support member axial surface 188.

Figure 6:
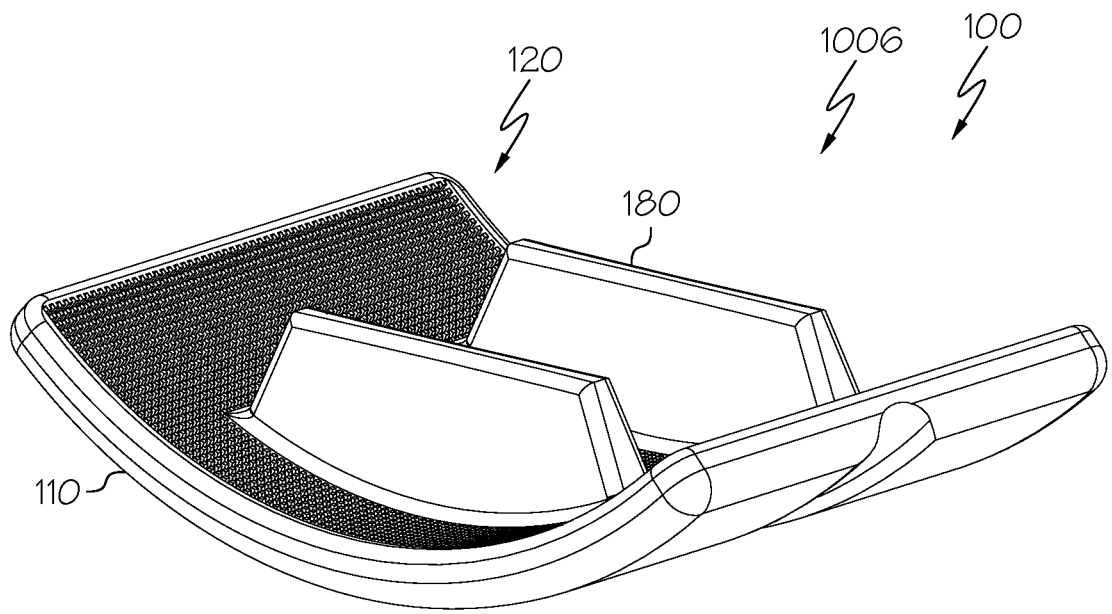
FIG. 6 is a perspective view of a hard-tissue implant corresponding to a talar implant for ankle.

With reference to FIG. 6, the talar implant for ankle 1006 exemplifies a hard-tissue implant 100 in which the support member 180 has (1) a support member height 186 that is greater than the height 420 of all of the pillars 140, (2) a support member axial surface 188 that is angled with respect to the face 120 of the hard-tissue implant 100, e.g. being generally transverse with respect to the face 120 of the hard-tissue implant 100, and (3) a support member axial surface 188 that lacks pillars. The talar implant for ankle 1006 also exemplifies a hard-tissue implant 100 including more than one support member 180. In this case the support members 180 correspond to keels.

Figure 7:
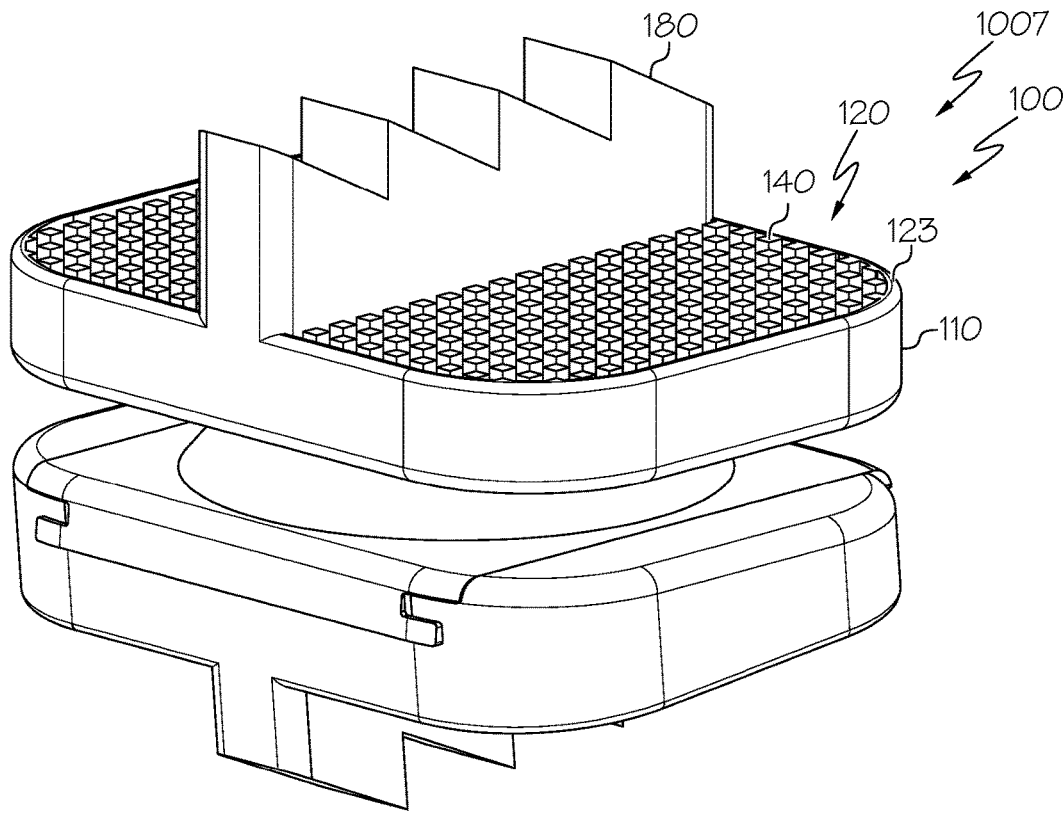
FIG. 7 is a perspective view of a hard-tissue implant corresponding to an artificial disc implant for spine.

With reference to FIG. 7, the artificial disc implant for spine 1007 exemplifies a hard-tissue implant 100 in which the support member 180 has (1) a support member height 186 that is greater than the height 420 of all of the pillars 140, (2) a support member axial surface 188 that is angled with respect to the face 120 of the hard-tissue implant 100, e.g. being generally transverse with respect to the face 120 of the hard-tissue implant 100, and (3) a support member axial surface 188 that lacks pillars. The artificial disc implant for spine 1007 also exemplifies a hard-tissue implant 100 including more than one support member 180. In this case the support members 180 correspond to keels. The artificial disc implant for spine 1007 also exemplifies a hard-tissue implant 100 including more than one face 120 including pillars 140. The artificial disc implant for spine 1007 also exemplifies a hard-tissue implant 100 in which the edge 130 includes a raised wall 123 that extends above the face 120, such that the face 120 is recessed with respect to the raised wall 123, and (2) the pillar height 420 is the same as a height of the raised wall 123.

Methods of Making Hard-Tissue Implants

Methods will now be described for making a hard-tissue implant that, upon implantation into a hard tissue, provides immediate load transfer and prevents stress shielding. The hard-tissue implant 100 is as described above.

The method includes a step of designing the hard-tissue implant 100 such that the ratio of (i) the product of (a) the Young's modulus of the hard-tissue implant 100 and (b) the sum of the volumes 520 of the pillars 140, to (ii) the product of (a) the Young's modulus of the hard tissue and (b) the sum of the volumes 710 of the slots 150, will be, for example, 0.80:1 to 3.8:1, 0.90:1 to 3.6:1, 0.85:1 to 1.6:1, 0.92:1 to 1.4:1, 2.2:1 to 3.7:1, or 2.4:1 to 3.5:1. Without wishing to be bound by theory, it is believed that by designing the hard-tissue implant 100 in this way the interface resulting from implantation of the hard-tissue implant 100 will have a Young's modulus of elasticity similar to that of the bulk hard tissue adjacent to the interface, and again will exhibit properties similar to those of the bulk hard tissue adjacent to the interface, e.g. high resilience to load. This step can be carried out, for example by determining the features of the hard-tissue implant 100 in view of the particular hard tissue that will be the object of implantation. Features to be determined include the material from which the hard-tissue implant 100 will be made, the dimensions of the bulk implant 110 of the hard-tissue implant 100, the area 170 of the face 120 of the hard-tissue implant 100 across which pillars 140 will be distributed, and the number, distribution, size, and direction of extension of the pillars 140.

The hard tissue can be selected, for example, from the group consisting of bone, cartilage, calcified cartilage, non-calcified cartilage, and tissue that has become mineralized. The hard tissue can also be selected, for example, from the group consisting of long bone, maxillary bone, mandibular bone, and membranous bone. The hard tissue can also be selected, for example, from the group consisting of shoulder, femur, tibia, and talus. The hard tissue can also be, for example, spine. The hard tissue can also be selected, for example, from spine.

The hard-tissue implant 100 can be made from one or more of the materials and/or hard tissues as described above. Also, the hard-tissue implant 100 can include the various example embodiments as disclosed above.

The Young's modulus of elasticity of the hard-tissue implant 100 can be extrapolated based on that of the materials and/or hard tissues from which the hard-tissue implant 100 is made, or determined experimentally. The Young's modulus of elasticity of the hard tissue can be determined, for example, based on previously determined values for hard tissue of that type or based on direct measurement. For example, it has been reported in the art that wet human femoral bone yields values for Young's modulus of elasticity, as determined by mechanical testing, as follows: $E_{long}$ 17 GPa, $E_{transv}$ 11.5, and $E_{transv}$ 11.5. See, e.g., Elastic anisotropy of bone, http://silver.neep.wisc.edu/~lakes/BME315N3.pdf (last accessed Dec. 8, 2010) (citing Reilly, D. T. & Burstein, A. H., The Elastic and Ultimate Properties of Compact Bone Tissue, 8 J. Biomechanics 393-405 (1975)). It has also been reported in the art that wet bovine femoral bone yields values for Young's modulus of elasticity, as determined by ultrasound, as follows: $E_{long}$ 22 GPa, $E_{transv}$ 15, and $E_{transv}$ 12. See, e.g., Elastic anisotropy of bone (citing Van Buskirk, W. C. & Ashman, R. B., The Elastic Moduli of Bone, in Mechanical Properties of Bone, Joint ASME-ASCE Applied Mechanics, Fluids Engineering and Bioengineering Conference, Boulder, Colo., 1981). It has also been reported in the art that the stiffness of compact bone tissue varies with the type of bone, e.g. the Young's moduli of fibular bone and tibial bone are about 18% greater and 7% greater, respectively, than the Young's modulus of femoral bone. See, e.g., Elastic anisotropy of bone.

Additional alternatives for the step of designing the hard-tissue implant 100 such that the ratio of (i) the product of (a) the Young's modulus of the hard-tissue implant 100 and (b) the sum of the volumes 520 of the pillars 140 to (ii) the product of (a) the Young's modulus of the hard tissue and (b) the sum of the volumes 710 of the slots 150 will be, for example, 0.80:1 to 3.8:1, 0.90:1 to 3.6:1, 0.85:1 to 1.6:1, 0.92:1 to 1.4:1, 2.2:1 to 3.7:1, or 2.4:1 to 3.5:1, can include, for example, use of different materials for making the hard-tissue implant 100, selecting different dimensions of the bulk implant 110 of the hard-tissue implant 100, selecting a different area 170 of the face 120 of the hard-tissue implant 100 across which pillars 140 will be distributed, and/or selecting different numbers, distributions, sizes, and directions of extension of the pillars 140. For example, for design of a hard-tissue implant 100 made from a hard tissue, the relatively low Young's modulus of elasticity of the hard tissue could be taken into account, such that the hard-tissue implant 100 could be designed to yield an interface, upon implantation into a hard tissue, for which the ratio of (i) the sum of the volumes of the slots to (ii) the sum of the volumes of the pillars and the volumes of the slots is approximately 0.50:1 and the ratio of (i) the product of (a) the Young's modulus of the hard-tissue implant 100 and (b) the sum of the volumes 520 of the pillars 140 to (ii) the product of (a) the Young's modulus of the hard tissue and (b) the sum of the volumes 710 of the slots 150 will be about 1:1. Also for example, for design of a hard-tissue implant 100 for implantation into a relatively old hard tissue, e.g. a bone of an elderly person, a relative decrease in Young's modulus of elasticity associated with increasing age of a hard tissue can be taken into account in designing the hard-tissue implant 100.

The method also includes a step of making the hard-tissue implant 100 in accordance with the design. Methods for making a hard-tissue implant 100 as disclosed herein include laser cutting, injection molding, 3D printing, and other fabrication methods that are known in the art.

Methods of Using Hard-Tissue Implants

Methods will now be described for use of a hard-tissue implant 100 in a hard tissue of an individual in need thereof. The hard-tissue implant 100 is as described above.

The method includes a step of selecting the hard-tissue implant 100 such that the ratio of (i) the product of (a) the Young's modulus of the hard-tissue implant 100 and (b) the sum of the volumes 520 of the pillars 140, to (ii) the product of (a) the Young's modulus of the hard tissue and (b) the sum of the volumes 710 of the slots 150, is, for example, 0.80:1 to 3.8:1, 0.90:1 to 3.6:1, 0.85:1 to 1.6:1, 0.92:1 to 1.4:1, 2.2:1 to 3.7:1, or 2.4:1 to 3.5:1.

The method also includes a step of implanting the hard-tissue implant 100 in the hard-tissue. The implanting can be done, for example, without rotation or twisting of the hard-tissue implant 100. The implanting can also be done, for example, without use of adhesives, e.g. cement or grout. The implanting can also be done, for example, without use of screws or plating mechanisms.

The implanting can include, for example, pressing the hard-tissue implant 100 into the hard tissue, thereby providing immediate load transfer and preventing stress shielding. The pressing can be, for example, by direct compression, mechanical compression, or tapping. Such pressing can include pressing the pillars 140 and the at least one support member 180 of the hard-tissue implant 100 into the hard tissue, such that the pillars 140 and the at least one support member 180 penetrate into the hard tissue, partially or completely. For example, the hard-tissue implant 100 can be pressed into the hard-tissue such that the pillars 140 penetrate the hard-tissue to a depth of, for example, 1 to 10,000 µm, 100 to 5,000 µm, 200 to 2,500 µm, 300 to 1,000 µm, 400 to 600 µm, 450 to 550 µm, 490 to 510 µm, or 500 µm. Also for example, the hard-tissue implant 100 can be pressed into the hard-tissue such that pillars 140 penetrate the hard tissue to a depth, relative to the pillar height 420 of the pillars 140, of for example 25%, 50%, 75%, and 100% of the pillar height 420 of the pillars 140.

The implanting can also include, for example, pressing the hard-tissue implant 100 into the hard tissue, such that the pillars 140 are oriented perpendicularly to the primary axis of tension and compression of the hard tissue and penetrate the hard tissue, thereby providing immediate load transfer and preventing stress shielding. The term "primary axis of tension and compression of the hard tissue," as used herein, means the main axis of the hard tissue along which forces of tension and compression are transmitted during normal function and use of the hard tissue, e.g. the long axis of a bone such as tibia or femur. Without wishing to be bound by theory, it is believed that by having the pillars 140 oriented perpendicularly to the primary axis of tension and compression of the hard tissue, and further by having the pillars 140 penetrate the hard tissue during the implanting, that immediately following the implanting the hard-tissue implant 100 will experience immediate load transfer with respect to tension and compression of the hard tissue, and that this will prevent stress shielding of the hard tissue at the interface of the hard-tissue implant 100 and the hard tissue.

Also for example, the implanting can include pressing the hard-tissue implant 100 into the hard tissue, such that the pillars 140 are oriented at an acute angle relative to the direction of the pressing and penetrate the hard tissue, thereby providing immediate load transfer and preventing stress shielding. By the pillars 140 being oriented at an acute angle relative to the direction of the pressing it is meant that pillars 140 are angled forward to at least some extent, i.e. are at an angle of less than 90°, relative to the direction of the path by which the implant 100 is pressed into the hard tissue. By being oriented at an acute angle, it is meant that a plurality of pillars 140, e.g. at least 10%, at least 20%, at least 30%, at least 40%, at least 50%, at least 60%, at least 70%, at least 80%, at least 90%, or 100%, are oriented at an acute angle, e.g. at angles ranging from 1° to 89°, 10° to 80°, 20° to 70°, 30° to 60°, 40° to 50°, 1° to 10°, 11° to 20°, 21° to 30°, 31° to 40°, 41° to 50°, 51° to 60°, 61° to 70°, 71° to 80°, 81° to 89°, 15°, 30°, 45°, 60°, or 75°, relative to the direction of the pressing. Without wishing to be bound by theory, it is believed that by having the pillars 140 oriented at an acute angle relative to the direction of the pressing, and further by having the pillars 140 penetrate the hard tissue during the implanting, that again immediately following the implanting the hard-tissue implant 100 will experience immediate load transfer with respect to tension and compression of the hard tissue, thereby providing immediate load transfer between the hard-tissue implant 100 and the hard tissue, and that this will prevent stress shielding of the hard tissue at the interface of the hard-tissue implant 100 and the hard tissue.

Also for example, the implanting can include pressing the hard-tissue implant 100 into a cavity that has been milled in the hard tissue, such that the pillars 140 penetrate the hard tissue, thereby providing immediate load transfer and preventing stress shielding. For example, the cavity can be milled to dimensions wider than that of the bulk implant 110 but narrower than the bulk implant 110 including the pillars 140, such that the pressing of the hard-tissue implant 100 into the cavity results in the pillars 140 of the hard-tissue implant 100 contacting and penetrating the hard tissue during the pressing. Also for example, the cavity that has been milled in the hard tissue can be tapered from the surface of the hard tissue inward, i.e. wider at the surface of the hard tissue and narrower with increasing depth in the hard tissue, such that the pressing of the hard-tissue implant 100 into the cavity results in the pillars 140 of the hard-tissue implant 100 contacting and penetrating the hard tissue only after the implant 100 has been pressed to some depth in the cavity. Also for example, the hard-tissue implant 100 can be tapered, such that a tapered cavity and a tapered hard-tissue implant 100 have a complementary fit, e.g. such that pressing of the hard-tissue implant 100 into the cavity results in the pillars 140 of the hard-tissue implant 100 contacting and penetrating the hard tissue only after the implant 100 has been pressed to some depth in the cavity at each area of complementary fit between the tapered cavity and the tapered hard-tissue implant 100. Without wishing to be bound by theory, it is believed that by pressing the hard-tissue implant 100 into a cavity that has been milled in the hard tissue, such that the pillars 140 penetrate the hard tissue during the implanting, that again immediately following the implanting the hard-tissue implant 100 will experience immediate load transfer with respect to tension and compression of the hard tissue, and that this will prevent stress shielding of the hard tissue at the interface of the hard-tissue implant 100 and the hard tissue.

In some embodiments, additional hard tissue can be added to the face 120 and/or the pillars 140 of the hard-tissue implant 100 prior to implanting. For example, shavings of hard-tissue of a patient, generated during preparation work including sawing or drilling of hard tissue of the patient, can be added. This may promote growth of tissue into slots 150 of the hard-tissue implant 100 following implantation.

Also in some embodiments, additional compositions can be added to the face 120 and/or the pillars 140 of the hard-tissue implant 100 prior to implanting. Such compositions include, for example, blood, one or more antibiotics, one or more osteogenic compounds, bone marrow aspirate, and/or surface chemistry for inducing early bone ingrowth. For example, the face 120 and/or the pillars 140 can be coated with one or more such compositions, with the pillars 140 retaining the compositions during implantation. This also may promote growth of tissue into slots 150 of the hard-tissue implant 100 following implantation.

Standard approaches for implanting the hard-tissue implant 100, pressing the hard-tissue implant 100 into hard tissue, orienting the hard-tissue implant 100 or pillars 140 thereof, and pressing the hard-tissue implant 100 into a cavity that has been milled in the hard tissue are known in the art and can be used in the methods disclosed here.

The hard tissue can be selected, for example, from the group consisting of bone, cartilage, calcified cartilage, non-calcified cartilage, and tissue that has become mineralized. The hard tissue can also be selected, for example, from the group consisting of long bone, maxillary bone, mandibular bone, and membranous bone. The hard tissue can also be selected, for example, from the group consisting of shoulder, femur, tibia, and talus. The hard tissue can also be, for example, spine. The hard tissue can also be selected, for example, from spine.

The method can be applied to example embodiments of the hard-tissue implant 100 as disclosed above. The ratio of (i) the sum of the volumes 710 of the slots 150 to (ii) the sum of the volumes 520 of the pillars 140 and the volumes 710 of the slots 150 can be determined essentially as described above with respect to designing the hard-tissue implant 100. The ratio of (i) the product of (a) the Young's modulus of the hard-tissue implant 100 and (b) the sum of the volumes 520 of the pillars 140, to (ii) the product of (a) the Young's modulus of the hard tissue and (b) the sum of the volumes 710 of the slots 150, can also be determined essentially as described above with respect to designing the hard-tissue implant 100.

EXAMPLES

Pillar Design Variation and Underlying Anatomic Structures

A theory for variation of pillar design based on underlying anatomical structures is presented. In accordance with the theory, the pillar geometry or pillar material can be varied to produce a desired structural response when engaged with surrounding tissue, based on the specific orthopedic application and underlying anatomy. For example, cancellous bone exhibits a material modulus of approximately 0.04 to 1.0 GPa, while cortical bone exhibits a material modulus of approximately 12.0 to 25.0 GPa. In some applications it may be desirable and/or necessary to provide a single implant that can interface with both cancellous and cortical bone. For example, a tibial tray in a total knee arthrodesis (also termed TKA) may interface at its peripheral surface(s) with cortical bone while interfacing at its central surface(s) with cancellous bone. Also for example, a femoral capture implant for knee may interface at its peripheral surface(s) with cortical bone while interfacing at its central surface(s) with cancellous bone. To elicit the desired response and interaction between the implant and tissue, i.e. underlying cortical and cancellous bone, implant material and/or pillar geometry can be varied to provide the desired interface properties.

While the gross material properties (material modulus) define the response of the bulk material, the structural response of the specific design parameters can also affect the mechanical response of the pillars at the interface.

Consider, for example, two pillars, both having a width of 500 µm and a height of 2,000 µm, but having been made from two different implant materials, e.g. a metal corresponding to titanium alloy Ti-6Al-4V and a plastic corresponding to polyetheretherketone (PEEK). The modulus of titanium alloy Ti-6Al-4V is approximately 110 GPa, whereas the material modulus of PEEK is approximately 4.1 GPa. Given the same pillar geometry, the structural stiffness of the pillars will be much greater in titanium than PEEK.

Consider also two pillars made from the same material but differently sized, e.g. a first pillar having a width of 500 µm and a height of 500 µm, and a second pillar having a width of 500 µm and a height of 2,000 µm. While the two pillars have been made from the same base material with the same gross material properties, the two pillars will have very different structural stiffnesses in bending due to their different geometries. The taller pillars will be less stiff than the shorter pillars.

Now, considering the interface between the tissue, i.e. again underlying cortical and cancellous bone, and the implant, it is believed that it is advantageous to closely match the structural stiffness of the pillar geometry with the compliance of the underlying tissue, as indicated by the material modulus of the underlying tissue.

For example, an implant, such as a tibial tray in TKA, among others, can be made including two or more types of pillars, each type of pillar being made to have a geometry that will provide a structural stiffness that matches the compliance of the underlying tissue with which that type of pillar will interface. In this example, each type of pillar can be integral to the implant. One type of pillar can be positioned on one or more surfaces of the implant to interface with cortical bone, e.g. on one or more peripheral surfaces of the implant. Such pillars can be relatively short and more stiff, to match the compliance of the cortical bone. Another type of pillar can be positioned on one or more surfaces of the implant to interface with cancellous bone, e.g. on one or more central surfaces of the implant. Such pillars can be relatively tall and less stiff, to match the compliance of the underlying cancellous bone. Such implants may be made from one material and yet provide two or more types of pillars exhibiting different stiffnesses, each type of pillar being matched with the compliance of the underlying tissue.

Also for example, an implant, again such as a tibial tray in TKA, among others, can be made from two or more types of materials, one or more harder materials (higher gross material modulus) and one or more softer materials (lower gross material modulus). The harder material(s) can be used for pillars positioned on one or more surfaces of the implant to interface with cortical bone, e.g. one or more peripheral surfaces of the implant. The softer material(s) can be used for pillars positioned on one or more surfaces of the implant to interface with cancellous bone, e.g. one or more central surfaces of the implant.

Initial experiments have been conducted to test the theory. The initial experiments were conducted using a constant tissue substitute (15 PCF SawBones biomechanical test material) to simulate bone tissue. The tissue substitute is a foam. A variety of pillar geometries and implant materials were tested in a common test setup (ASTM Draft F-04.25.02.02 Static Expulsion) to quantify the interaction between the implants and the tissue substitute. Specifically, the experiments involved placement of implants between two pieces of tissue substitute, to form a "foam-pillar-foam sandwich," then measuring resistance to pushout (expulsion) of the implants from between the two pieces of tissue substitute.

Figure 52:
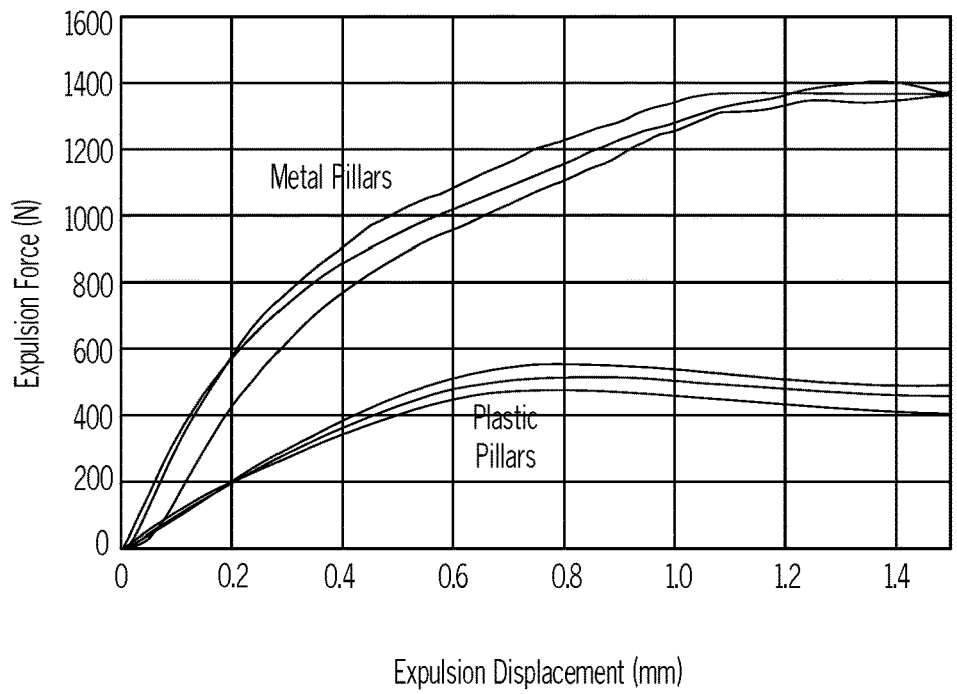
FIG. 52 shows results of an expulsion resistance test (Y-axis: expulsion force (N); X-axis: expulsion displacement (mm)) for implants including pillars having a pillar height of 2,000 μm and a pillar width of 500 μm, with the implants and pillars being made from materials as follows: metal pillars=titanium alloy Ti-6Al-4V; and plastic pillars=polyetheretherketone (PEEK)
Figure 53:
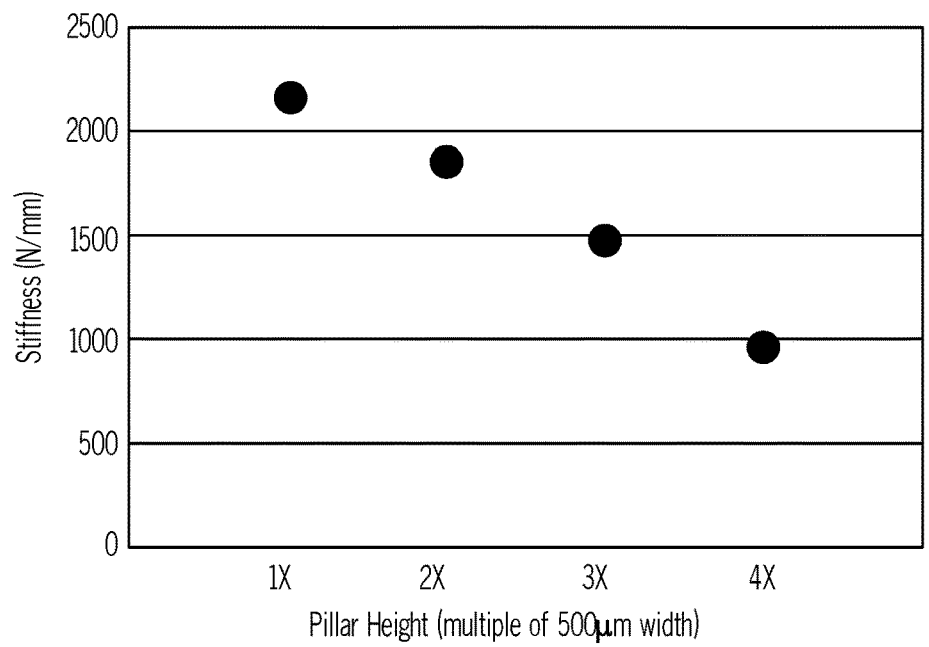
FIG. 53 shows results of a cage expulsion test (Y-axis: stiffness; X-axis: pillar height), for implants including pillars made from PEEK, each pillar having a pillar width of 500 μm, with pillar heights expressed as a multiple of pillar width as follows: 1×=pillar height 500 μm; 2×=pillar height 1,000 μm; 3×=pillar height 1,500 μm; and 4×=pillar height 2,000 μm.

Results of the initial experiments are provided in FIG. 52 and FIG. 53. FIG. 52 shows results of an expulsion resistance test for implants including pillars having a pillar height of 2,000 µm and a pillar width of 500 µm, with the pillars being integral to the implants, and with the implants and pillars being made from titanium alloy Ti-6Al-4V (metal pillars) or PEEK (plastic pillars). FIG. 53 shows results of a cage expulsion test for implants including pillars made from PEEK, with the pillars being integral to the implants, each pillar having a pillar width of 500 µm, and the pillars having pillar heights of 500 µm (1×), 1,000 µm (2×), 1,500 µm (3×), or 2,000 µm (4×).

It was found generally that pillars that are taller and/or made from softer material (lower gross material modulus) tended to provide a less stiff interface (lower force to displacement slope). Pillars that are shorter and/or made from a stronger material (higher gross material modulus) tended to provide an increased resistance to pushout (expulsion).

Considering the results in more detail, at early time points following placement of the implants between the two pieces of tissue substitute, before the pillars began to become embedded into the tissue substitute, the stiffness response indicated that increasing pillar height resulted in a "softer" stiffness response. At later time points following placement of the implants, as the pillars began to become embedded into the tissue substitute, the stiffness response changed. Pillars of 1,000 µm height exhibited increased resistance to pushout relative to pillars of 500 µm height, as the pillars of 1,000 µm height were strong enough to dig deeply into the tissue substitute and resist the expulsion force. In contrast, for pillars of 1,500 µm and 2,000 µm heights, the expulsion force exceeded the collective bending strength of the pillars, and the maximum expulsion force actually decreased because the pillars would bend before the pillars could fully embed and carry the greater expulsion force. Importantly, it is early time points that are clinically relevant. In vivo, a range of motion of about 0 to 500 µm would be expected to be relevant. Greater motion would likely be a clinical failure. Within the range of motion of 0 to 500 µm, stiffer material pillars provide greater expulsion resistance. Also, there is a trade-off between stiffness and strength. For the height parameter, stiffness is linear with height but there is a height where expulsion resistance is a maximum. Beyond that height, expulsion resistance falls off due to pillar bending failure.

Exemplary Embodiments

The following are exemplary embodiments of the hard-tissue implant, the method of making the hard-tissue implant, and the method of use of the hard-tissue implant as disclosed herein.

Embodiment A: A hard-tissue implant comprising:
(a) a bulk implant;
(b) a face being an exterior surface of the bulk implant;
(c) pillars for contacting a hard tissue, the pillars being distributed on the face, across an area of at least 30 mm², and extending distally therefrom, and each pillar being integral to the bulk implant, having a distal end, having a transverse area of (100×100) to (10,000×10,000) µm², and having a height of 100 to 10,000 µm;

(d) slots to be occupied by the hard tissue, the slots being defined by the pillars and each slot having a width of 100 to 10,000 µm as measured along the shortest distance between adjacent pillars; and (e) at least one support member for contacting the hard tissue, the at least one support member being positioned on the face among the pillars, extending distally from the face, and having a transverse area greater than the transverse area of any of the pillars; wherein:

the hard-tissue implant has a Young's modulus of elasticity of at least 3 GPa, and has a ratio of (i) the sum of the volumes of the slots to (ii) the sum of the volumes of the pillars and the volumes of the slots of 0.40:1 to 0.90:1.

Embodiment B: The hard-tissue implant of embodiment A, wherein the hard-tissue implant is made of one or more materials selected from implantable-grade polyaryletherketone that is essentially unfilled, implantable-grade polyetheretherketone, implantable-grade polyetherketoneketone, titanium, stainless steel, cobalt-chromium alloy, titanium alloy, Ti-6A1-4V titanium alloy, Ti-6A1-7Nb titanium alloy, ceramic material, silicon nitride (Si3N4), implantable-grade composite material, implantable-grade polyaryletherketone with filler, implantable-grade polyetheretherketone with filler, implantable-grade polyetheretherketone with carbon fiber, or implantable-grade polyetheretherketone with hydroxyapatite.

Embodiment C: The hard tissue implant of embodiment A, wherein the hard-tissue implant is made of one or more other hard tissues selected from human hard tissue, animal hard tissue, autologous hard tissue, allogenic hard tissue, xenogeneic hard tissue, human cartilage, animal cartilage, human bone, animal bone, cadaver bone, or cortical allograft.

Embodiment D: The hard tissue implant of embodiment A, wherein the hard-tissue implant is made of one or more materials selected from resin for rapid prototyping, SOMOS® NanoTool non-crystalline composite material, SOMOS® 9120 liquid photopolymer, SOMOS® WaterShed XC 11122 resin, ACCURA® XTREME™ White 200 plastic, or ACCURA® 60) plastic.

Embodiment E: The hard-tissue implant of any of embodiments A-D, wherein the face is flat.

Embodiment F: The hard-tissue implant of any of embodiments A-D, wherein the face has a cylindrical contour.

Embodiment G: The hard-tissue implant of any of embodiments A-F, wherein the pillars extend in a uniform direction.

Embodiment H: The hard-tissue implant of any of embodiments A-G, wherein the pillars are perpendicular to the face.

Embodiment I: The hard-tissue implant of any of embodiments A-H, wherein the transverse area of each pillar is (250×250) µm² to (1,000×1,000) µm².

Embodiment J: The hard-tissue implant of any of embodiments A-I, wherein the height of each pillar is 200 to 2,500 µm.

Embodiment K: The hard-tissue implant of any of embodiments A-J, wherein the width of each slot is 200 to 2,500 µm.

Embodiment L: The hard-tissue implant of any of embodiments A-K, wherein the Young's modulus of the hard-tissue implant is 18 to 25 GPa and the ratio of (i) the sum of the volumes of the slots to (ii) the sum of the volumes of the pillars and the volumes of the slots is 0.51:1 to 0.60:1.

Embodiment M: The hard-tissue implant of embodiments A-K, wherein the Young's modulus of the hard-tissue implant is 100 to 110 GPa and the ratio of (i) the sum of the volumes of the slots to (ii) the sum of the volumes of the pillars and the volumes of the slots is 0.72:1 to 0.76:1.

Embodiment N: The hard-tissue implant of any of embodiments A-K, wherein the hard-tissue implant is made of implantable-grade polyetheretherketone with filler, the transverse area of each pillar is (350×350) to (450×450) µm², the height of each pillar is 400 to 600 µm, the width of each slot is 190 to 210 µm, and the ratio of the sum of (i) the volumes of the slots to (ii) the sum of the volumes of the pillars and the volumes of the slots is 0.51:1 to 0.60:1.

Embodiment O: The hard-tissue implant of any of embodiments A-K, wherein the hard-tissue implant is made of titanium, the transverse area of each pillar is (350×350) to (450×450) µm², the height of each pillar is 400 to 600 µm, the width of each slot is 390 to 410 µm, and the ratio of (i) the sum of the volumes of the slots to (ii) the sum of the volumes of the pillars and the volumes of the slots is 0.72:1 to 0.76:1.

Embodiment P: The hard-tissue implant of any of embodiments A-O, wherein the at least one support member comprises at least two support members.

Embodiment Q: The hard-tissue implant of any of embodiments A-P, wherein the at least one support member is integral to the bulk implant.

Embodiment R: The hard-tissue implant of any of embodiments A-Q, wherein the at least one support member comprises a support member axial surface comprising support member pillars extending therefrom.

Embodiment S: The hard-tissue implant of any of embodiments A-Q, wherein the at least one support member comprises a support member axial surface lacking pillars.

Embodiment T: The hard-tissue implant of any of embodiments A-S, wherein the bulk implant is non-porous.

Embodiment U: The hard-tissue implant of any of embodiments A-T, wherein the pillars are non-porous.

Embodiment V: The hard-tissue implant of any of embodiments A-U, wherein the at least one support member is non-porous.

Embodiment W: The hard-tissue implant of any of embodiments A-V, wherein one or more pillars have dimensions that differ from those of other pillars, such that the transverse areas and/or heights, and thus volumes, of the one or more pillars differ from those of the other pillars.

Embodiment X: The hard-tissue implant of embodiment W, wherein the one or more pillars are distributed peripherally with respect to the face and are intended for insertion into cortical bone, and the other pillars are distributed centrally with respect to the face and are intended for insertion into cancellous bone.

Embodiment Y: The hard-tissue implant of any of embodiments A-X, wherein the hard-tissue implant is selected from the group consisting of a glenoid implant for shoulder, a distal radius plate implant for wrist, a femoral capture implant for knee, a tibial implant for knee, a tibial implant for ankle, a talar implant for ankle, and an artificial disc implant for spine.

Embodiment Z: A method of making the hard-tissue implant of any of embodiments A-Y, that, upon implantation into a hard tissue, provides immediate load transfer and prevents stress shielding, the method comprising:

(1) designing the hard-tissue implant such that the ratio of (i) the product of (a) the Young's modulus of the hard-tissue implant and (b) the sum of the volumes of the pillars to (ii) the product of (a) the Young's modulus of the hard tissue and (b) the sum of the volumes of the slots will be 0.80:1 to 3.8:1; and (2) making the hard-tissue implant.

Embodiment AA: A method of use of the hard-tissue implant of any of embodiments A-Y in a hard tissue of an individual in need thereof, the method comprising:

(1) selecting the hard-tissue implant such that the ratio of (i) the product of (a) the Young's modulus of the hard-tissue implant and (b) the sum of the volumes of the pillars to (ii) the product of (a) the Young's modulus of the hard tissue and (b) the sum of the volumes of the slots is 0.80:1 to 3.8:1; and (2) implanting the hard-tissue implant in the hard-tissue of the individual.

It will be apparent to those skilled in the art that various modifications and variations can be made without departing from the spirit and scope of the claimed invention.

What is claimed is:

1. A femoral capture implant for knee comprising:
   (a) a bulk implant;
   (b) at least three adjoined planar faces defining an exterior bone-engaging surface of the bulk implant, the exterior bone-engaging surface sized and configured to contact a resected surface of a distal femur;
   (c) pillars for contacting a hard tissue, the pillars being distributed on the exterior bone-engaging surface, across an area of at least 30 mm$^2$, and extending perpendicularly from each of the at least three adjoined planar faces, and each pillar being integral to the bulk implant, having a distal end, having a transverse area of $(100\times100)$ μm$^2$ to $(10,000\times10,000)$ μm$^2$, and having a height of 100 μm to 10,000 μm;
   (d) slots to be occupied by the hard tissue, the slots being defined by the pillars and each slot having a width of 100 μm to 10,000 μm as measured along the shortest distance between adjacent pillars; and
   (e) at least one support member for contacting the hard tissue, the at least one support member being positioned on the exterior bone-engaging surface among the pillars, extending distally from the exterior bone-engaging surface, having a transverse area greater than the transverse area of any of the pillars, and having a height greater than the height of any of the pillars;
   wherein the femoral capture implant has a Young's modulus of elasticity of at least 3 GPa, and has a ratio of (i) the sum of the volumes of the slots to (ii) the sum of the volumes of the pillars and the volumes of the slots of 0.40:1 to 0.90:1;
   wherein:
      one or more pillars have dimensions that differ from those of other pillars, such that the transverse areas and/or heights, and thus volumes, of the one or more pillars differ from those of the other pillars; and
      the one or more pillars are distributed peripherally with respect to the exterior bone-engaging surface and are intended for insertion into cortical bone, and the other pillars are distributed centrally with respect to the exterior bone-engaging surface and are intended for insertion into cancellous bone; and
   wherein the pillars are non-porous.

2. The femoral capture implant for knee of claim 1, wherein the femoral capture implant for knee is made of one or more materials selected from implantable-grade polyaryletherketone that is essentially unfilled, implantable-grade polyetheretherketone, implantable-grade polyetherketoneketone, titanium, stainless steel, cobalt-chromium alloy, titanium alloy, Ti-6Al-4V titanium alloy, Ti-6Al-7Nb titanium alloy, ceramic material, silicon nitride (Si3N4), implantable-grade composite material, implantable-grade polyaryletherketone with filler, implantable-grade polyetheretherketone with filler, implantable-grade polyetheretherketone with carbon fiber, or implantable-grade polyetheretherketone with hydroxyapatite.

3. The femoral capture implant for knee of claim 1, wherein the femoral capture implant for knee is made of one or more hard tissues selected from human hard tissue, animal hard tissue, autologous hard tissue, allogenic hard tissue, xenogeneic hard tissue, human cartilage, animal cartilage, human bone, animal bone, cadaver bone, or cortical allograft.

4. The femoral capture implant for knee of claim 1, wherein the femoral capture implant for knee is made of one or more materials selected from resin for rapid prototyping, SOMOS® NanoTool non-crystalline composite material, SOMOS® 9120 liquid photopolymer, SOMOS® WaterShed XC 11122 resin, ACCURA® XTREME™ White 200 plastic, or ACCURA® 60) plastic.

5. The femoral capture implant for knee of claim 1, wherein the transverse area of each pillar is $(250\times250)$μm$^2$ to $(1,000\times1,000)$μm$^2$.

6. The femoral capture implant for knee of claim 1, wherein the height of each pillar is 200 to 2,500 μm.

7. The femoral capture implant for knee of claim 1, wherein the width of each slot is 200 to 2,500 μm.

8. The femoral capture implant for knee of claim 1, wherein the at least one support member is integral to the bulk implant.

9. The femoral capture implant for knee of claim 1, wherein the at least one support member comprises a support member axial surface comprising support member pillars extending therefrom.

10. The femoral capture implant for knee of claim 1, wherein the at least one support member comprises a support member axial surface lacking pillars.

11. The femoral capture implant for knee of claim 1, wherein the bulk implant is non-porous.

12. The femoral capture implant for knee of claim 1, wherein the at least one support member is non-porous.

* * * * *

UNITED STATES PATENT AND TRADEMARK OFFICE
CERTIFICATE OF CORRECTION

PATENT NO. : 11,213,398 B2  
APPLICATION NO. : 16/492285  
DATED : January 4, 2022  
INVENTOR(S) : George J. Picha et al.

Page 1 of 1

It is certified that error appears in the above-identified patent and that said Letters Patent is hereby corrected as shown below:

In the Specification

Column 13, Line 2, the text "$2.5 \times 10^8$ (v)" should read -- $2.5 \times 10^8$ µm³, (v) --.

Signed and Sealed this  
Twenty-sixth Day of July, 2022

Katherine Kelly Vidal  
*Director of the United States Patent and Trademark Office*